United States Patent
Schmidt et al.

(10) Patent No.: US 9,150,598 B2
(45) Date of Patent: Oct. 6, 2015

(54) MASKING APERTURES ENABLING AUTOMATION AND SOLUTION EXCHANGE IN SESSILE BILAYERS

(71) Applicants: Jacob J. Schmidt, Sherman Oaks, CA (US); Shiva Portonovo, West Hollywood, CA (US); Jason L. Poulos, Los Angeles, CA (US)

(72) Inventors: Jacob J. Schmidt, Sherman Oaks, CA (US); Shiva Portonovo, West Hollywood, CA (US); Jason L. Poulos, Los Angeles, CA (US)

(73) Assignees: The Regents of the University of California, Oakland, CA (US); Librede, Inc., Sherman Oaks, CA (US)

( * ) Notice: Subject to any disclaimer, the term of this patent is extended or adjusted under 35 U.S.C. 154(b) by 196 days.

(21) Appl. No.: 13/646,305

(22) Filed: Oct. 5, 2012

(65) Prior Publication Data
US 2013/0147461 A1    Jun. 13, 2013

Related U.S. Application Data

(60) Provisional application No. 61/543,771, filed on Oct. 5, 2011.

(51) Int. Cl.
| | | |
|---|---|---|
| G01R 19/00 | (2006.01) | |
| C07F 9/22 | (2006.01) | |
| G01N 27/00 | (2006.01) | |
| A61K 9/127 | (2006.01) | |
| G01N 33/487 | (2006.01) | |

(52) U.S. Cl.
CPC . *C07F 9/22* (2013.01); *A61K 9/127* (2013.01); *G01N 27/00* (2013.01); *G01N 33/48728* (2013.01)

(58) Field of Classification Search
None
See application file for complete search history.

(56) References Cited

U.S. PATENT DOCUMENTS

| | | | |
|---|---|---|---|
| 3,846,795 A | 11/1974 | Jones | |
| 5,961,832 A | 10/1999 | Shaw et al. | 210/634 |
| 6,436,905 B1 | 8/2002 | Tonge et al. | |
| 6,682,893 B2 | 1/2004 | Taylor et al. | |
| 6,699,952 B2 | 3/2004 | Chaikof et al. | |
| 6,835,313 B2 | 12/2004 | Sando et al. | 210/634 |
| 6,846,352 B2 | 1/2005 | Yatake | |
| 6,846,795 B2 | 1/2005 | Lant et al. | |
| 6,849,426 B2 | 2/2005 | Chen et al. | |
| 6,852,816 B2 | 2/2005 | Lewis et al. | |

(Continued)

FOREIGN PATENT DOCUMENTS

| | | |
|---|---|---|
| EP | 2293921 A1 | 3/2011 |
| EP | 2521650 A1 | 11/2012 |

(Continued)

OTHER PUBLICATIONS

Akeson et al., "Microsecond Time-Scale Discrimination Among Polycytidylic Acid, Polyadenylic Acid, and Polyuridylic Acid as Homopolymers or as Segments Within Single RNA Molecules," *Biophys J* 1999, 77:3227-3233.

(Continued)

*Primary Examiner* — Minh N Tang
(74) *Attorney, Agent, or Firm* — Ballard Spahr LLP

(57) ABSTRACT

Disclosed herein are devices and methods related to the production and measurements of amphiphilic molecule bilayers, which are useful in high throughput electrophysiological screening and ion channel measurement in bilayers. This abstract is intended as a scanning tool for purposes of searching in the particular art and is not intended to be limiting of the present invention.

7 Claims, 16 Drawing Sheets

(56) References Cited

U.S. PATENT DOCUMENTS

| | | | |
|---|---|---|---|
| 6,863,833 B1* | 3/2005 | Bloom et al. | 216/2 |
| 6,913,697 B2 | 7/2005 | Lopez et al. | |
| 7,201,836 B2 | 4/2007 | Vogel et al. | |
| 7,479,483 B2 | 1/2009 | Ponzoni et al. | |
| 7,638,092 B2* | 12/2009 | Ide | 422/504 |
| 7,939,270 B2* | 5/2011 | Holden et al. | 435/7.1 |
| 8,038,885 B2 | 10/2011 | Schmidt et al. | |
| 8,242,077 B2 | 8/2012 | Lakey et al. | |
| 2002/0081617 A1 | 6/2002 | Buranda et al. | |
| 2002/0158016 A1 | 10/2002 | Norberg et al. | 210/634 |
| 2003/0044455 A1 | 3/2003 | Kazakov et al. | 424/450 |
| 2003/0096418 A1 | 5/2003 | Yamazaki et al. | |
| 2003/0175824 A1 | 9/2003 | Pishko et al. | |
| 2005/0112184 A1 | 5/2005 | Jahn et al. | |
| 2005/0154374 A1 | 7/2005 | Hunter et al. | |
| 2005/0194316 A1 | 9/2005 | Pourahmadi et al. | 210/638 |
| 2006/0003097 A1 | 1/2006 | Andres et al. | |
| 2006/0029955 A1 | 2/2006 | Guia et al. | |
| 2006/0094119 A1 | 5/2006 | Ismagilov et al. | |
| 2006/0160066 A1 | 7/2006 | Bhatia et al. | |
| 2009/0170118 A1* | 7/2009 | Schmidt et al. | 435/7.1 |
| 2011/0111985 A1 | 5/2011 | Lakey et al. | |
| 2011/0118489 A1 | 5/2011 | Schmidt et al. | |
| 2011/0120871 A1* | 5/2011 | Reid et al. | 204/540 |
| 2012/0025414 A1 | 2/2012 | Schmidt et al. | |
| 2013/0056358 A1 | 3/2013 | Poulos et al. | |

FOREIGN PATENT DOCUMENTS

| | | |
|---|---|---|
| EP | 2578207 A2 | 4/2013 |
| WO | WO-01/20330 A1 | 3/2001 |
| WO | WO-03/086197 A1 | 10/2003 |
| WO | WO-2007/028003 A2 | 3/2007 |
| WO | WO-2007/047498 A2 | 4/2007 |
| WO | WO-2009/143425 A1 | 11/2009 |
| WO | WO-2011/085047 A1 | 7/2011 |

OTHER PUBLICATIONS

Albertero, et al., "The α, α-(1 → 1) Linkage of Trehalose is Key to Anhydrobiotic Preservation," *J. Am Chem Soc* 2007, 129(34):10567-10574.

Alexandridis, "Amphiphilic copolymers and their applications," *Curr Opin Colloid Interface Sci* 1996, 1(4):490-501.

Andersson, et al., "TRPM8 Activation by Menthol, Icilin, and Cold is Differentially Modulated by Intracellular pH," *J Neurosci* 2004, 24:5364-5369.

Anrather et al., "Supported Membrane Nanodevices," *J Nanosci Nanotech* 2004, 4(1/2):1-22.

Baaken, et al., "Nanopore-Based Single-Molecule Mass Spectrometry on a Lipid Membrane Microaaray," *ACS Nano* 2011, 5:8080-8088.

Baaken, et al., "Planar microelectrode-cavity array for high-resolution and parallel electrical recording of membrane ionic currents," *Lab Chip* 2008, 8:938-944.

Bainbridge et al., "Voltage gating is a fundamental feature of porin and toxin beta-barrel membrane channels," *FEBS Lett* 1998, 431(3):305-308.

Bautista et al., "The menthol receptor TRPM8 is the principal detector of environmental cold," *Nature* 2007, 448:204-208.

Bayley et al., "Droplet interface bilyaers," *Mol Biosyst* 2008, 4:1191-1208.

Bayley et al., "Stochastic sensors inspired by biology," *Nature* 2001, 413(6852):226-230.

Beddow et al., "Reconstitution of nicotinic acetylcholine receptors into gel-protected lipid membranes," *Anal Chem* 2004, 76(8):2261-2265.

Behrendt et al., "Characterization of the mouse cold-menthol receptor TRPM8 and vanilloid receptor type-1 VR1 using a fluorometric imaging plate reader (FLIPR) assay," *Br J Pharmacol* 2004, 141:737-745.

Blake et al., "Monitoring chemical reactions by using ion-channel-forming peptides," *Chembiochem* 2006, 7:433-435.

Blaustein et al., "Anthrax Toxin—Channel-Forming Activity of Protective Antigen in Planar Phospholipid-Bilayers," *Proc Natl Acad Sci USA* 1989, 86:2209-2213.

Braha et al., "Designed protein pores as components for biosensors," *Chemistry and Biology* 1997, 4:497-505.

Braha et al., "Simultaneous stochastic sensing of divalent metal ions," *Nature Biotechnology* 2000, 18:1005-1007.

Brauchi et al., "Clues to understanding cold sensation: Thermodynamics and electrophysiological analysis of the cold receptor TRPM8," *Proc Natl Acad Sci USA* 2004, 101:15494-15499.

Brohawn et al., "Crystal structure of the human K2P TRAAK, a lipid- and mechano-sensitive K+ ion channel," *Science* 2012, 335(6067):436-441.

Canal et al., "Correlation between mesh size and equilibrium degree of swelling of polymeric networks," *J Biomed Mater Res* 1989, 23(10):1183-93.

Capone et al., "Designing Nanosensors Based on Charged Derivatives of Gramicidin A," *J Am Chem Soc* 2007, 129:9737-9745.

Chachin et al., "Epinastine, a nonsedating histamine H1 receptor antagonist, has a negligible effect on HERG channel," *Eur J Pharmacol* 1999, 374(3):457-460.

Cheley et al., "Stochastic sensing of nanomolar inositol 1,4,5-trisphosphate with an engineered pore," *Chem Biol* 2002, 9:829-838.

Chen et al., "Position of aromatic residues in the S6 domain, not inactivation, dictates cisapride sensitivity of HERG and eag potassium channels," *Proc Natl Acad Sci* 2002, 99(19):12461-12466.

Cheng et al., "A high-throughput HERG potassium channel function assay: An old assay with a new look," *Drug Dev Indust Pharm* 2002, 28(2):177-191.

Chiu et al., "Validation of a [3H]astemizole binding assay in HEK293 cells expressing HERG K+ channels," *J Pharmacol Sci* 2004, 95(3):311-319.

Chuang et al., "The super-cooling agent icilin reveals a mechanism of coincidence detection by a temperature-sensitive TRP channel," *Neuron* 2004, 43:859-869.

Cohen, "Fusion of phospholipid vesicles with planar phospholipid bilayer membranes. II. Incorporation of a vesicular membrane marker into the planar membrane," *J Gen Physiol* 1980, 75:251-270.

Colburn et al., "Attenuated cold sensitivity in TRPM8 null mice," *Neuron* 2007, 54:379-386.

Comley, "Patchers verses screener: divergent opinion on high throughput electro-physiology," *Drug Discovery World* 2003, 47-57.

Costello et al., "Improved gel-protected bilayers," *Biosensors Bioelectronics* 1999, 14(3):265-271.

Diaz et al., "The [3H]dofetilide binding assay is a predictive screening tool for hERG blockade and proarrhythmia: Comparison of intact cell and membrane preparations and effects of altering [K+]," *J Pharmacol Toxicol Methods* 2004, 50(3):187-199.

Dragoni et al., "The Cold and Menthol Receptor TRPM8 Contains a Functionally Important Double Cysteine Motif," *J Biol Chem* 2006, 281:37353-37360.

Dunlop et al., "High-throughput electrophysiology: an emerging paradigm for ion-channel screening and physiology," *Nature Reviews Drug Discovery* 2008, 7:358-368.

Eccles, "Methanol and related cooling compounds," *J Pharm Pharmacol* 1994, 46:618-630.

El-Arabi et al., "Ion channel drug potency assay with an artificial bilayer chip," Lab Chip 2012, 12(13):2409-2413.

Falconer et al., "High-Throughput Screening for Ion Channel Modulators," *J Biomolec Screen* 2002, 7(5):460-465.

Favero et al., "Membrane supported lipid bilayer membranes array: preparation, stability and ion-channel insertion," *Analytica Chimica Acta* 2002, 460(1):23-34.

Fernández et al., "Voltage—and cold-dependent gating of single TRPM8 ion channels," *J Gen Physiol* 2011, 137:173-195.

Funakoshi et al., "Lipid bilayer formation by contacting monolayers in a microfluidic device for membrane protein analysis," *Anal Chem* 2006, 78:8169-8174.

Golowasch et al., "Allosteric effects of Mg2+ on the gating of Ca2+-activated K+ channels from mammalian skeletal muscle," *J Exp Biol* 1986, 124(1):5-13.

(56) References Cited

OTHER PUBLICATIONS

Gu et al., "Stochastic sensing of organic analytes by a pore-forming protein containing a molecular adapter," Nature 1999, 398:686-690.
Guan et al., "Stochastic sensing of TNT with a genetically engineered pore," Chembiochem 2005, 6:1875-1881.
Han et al., "Nanopore Arrays for Stable and Functional Free-Standing Lipid Bilayers," *Adv Mater* 2007, 19:4466-4470.
Hancox et al., "The hERG potassium channel and hERG screening for drug-induced torsades de pointes," Pharmacol Therapeut 2008, 119(2):118-132.
Hanke & Schlue, "Planar Lipid Bilayers: Methods and Applications," *Academic Press, London; New York* 1993.
Hartgerink et al., "Self-Assembly and Mineralization of Peptide-Amphiphile Nanofibers," Science 2001, 294(5547):1684-1688.
Hartgerink et al., "Supramolecular Chemistry and Self-assembly Special Feature: Peptide-amphiphile nanofibers: A versatile scaffold for the preparation of self-assembling materials," Proc Natl Acad Sci 2002, 99(8):5133-5138.
Heron et al., "Direct detection of membrane channels from gels using water-in-oil droplet bilayers," J Am Chem Soc 2007, 129(51):16042-16047.
Hertzberg & Pope, "High-throughput screening: new technology for the 21st century," *Curr Opin Chem Biol* 2000, 4:445-451.
Hirano et al., "Lipid Bilayers at Gel/Gel Interface for Ion Channel Recordings," J Surf Sci Nanotech 2008, 6:130-133.
Holden et al., "Functional bionetworks from nanoliter water droplets," J Am Chem Soc 2007, 129:8650-8655.
Hromada et al., "Single molecule measurements within individual membrane-bound ion channels using a polymer-based bilayer lipid membrane chip," Lab Chip 2008, 8:602-608.
Hu et al., "2-Aminoethoxydiphenyl borate is a common activator of TRPV1, TRPV2, and TRPV3," J Biol Chem 2004, 279:35741-35748.
Hwang et al., "Asymmetric droplet interface bilayers," J Am Chem Soc 2008, 130:5878-5879.
Ide et al., "Lipid Bilayers at the Gel Interface for Single Ion Channel Recordings," Anal Chem 2008, 80(20):7792-7795.
Ide et al., "An Artificial Lipid Bilayer Formed on an Agarose-Coated Glass for Simultaneous Electrical and Optical Measurement of Single Ion Channels," *Biochem Biophys Res Commun* 1999, 265:595-599.
Ide et al., "Simultaneous Optical and Electrical Recording of a Single Ion-Channel," Japanese J Physiol 2002, 52:429-434.
Ionescu-Zanetti et al., "Mammalian electrophysiology on a microfluidic platform,"*Proc Natl Acad Sci USA* 2005, 102: 9112-9117.
Jacobson et al., "Microchip structures for submillisecond electrophoresism" *Analytical Chemistry* (1998) 70, 3476.
Jeon et al., "Long term storable and shippable liquid bilayer membrane platform," Lab Chip 2008, 8:1742-1744.
Jeon et al., "Black lipid membranes stabilized through substrate conjugation to a hydrogel," Biointerphases 2008, 3:96-100.
Jeon et al., "Hydrogel-Encapsulated Lipid Membranes," J Am Chem Soc 2006, 128(1):42-43.
Joanicot et al., "Droplet control for microfluidics," Science 2005, 309(5726):887-888.
Kang et al., "A Storable Encapsulated Bilayer Chip Containing a Single Protein Nanopore," *J Am Chem Soc* 2007, 129(15):4701-4705.
Kasianowicz et al., "Characterization of individual polynucleotide molecules using a membrane channel," *Proc Natl Acad Sci USA* 1996, 93, 13770-13773.
Kazakov et al., "UV-induced gelation on nanometer scale using liposome reactor," *Macromolecules* 2002, 35(5):1911-1920.
Keating et al., "Molecular and Cellular Mechanisms of Cardiac Arrhythmias," Cell 2001, 104:569-580.
Kedei et al., "Analysis of the native quaternary structure of vanilloid receptor 1," *J Biol Chem* 2001, 276:28613-28619.

Kiehn et al., "Cellular and Molecular Cardiology: Molecular Physiology and Pharmacology of HERG: Single-Channel Currents and Block by Dofetilide," *Circulation* 1996, 94(10):2572-2579.
Kloxin et al., "Photodegradable Hydrogels for Dynamic Tuning of Physical and Chemical Properties," Science 2009, 324(5923):59-63.
Knoll et al., "Functional tethered lipid bilayers," *Rev Mol Biotech* 2000, 74(3):137-158.
Krishna et al. "Tethered Bilayer Membranes Containing Ionic Reservoirs: Selectivity and Conductance," *Langmuir* 2003, 19:2294-2305.
Kuhner et al., "Lipid mono-and bilayer supported on polymer films: composite polymer-lipid films on solid substrates," *Biophys J* 1994, 67(1):217-226.
Lashinger et al., "AMTB, a TRPM8 channel blocker: evidence in rats for activity in overactive bladder and painful bladder syndrome," *Am J Physiol Renal Physiol* 2008, 295:803-810.
Le Pioufle et al., "Lipid bilayer microarray for parallel recording of transmembrane ion currents," Anal Chem 2008, 80:328-332.
Lee et al., "Photoreversible viscosity changes and gelation in mixtures of hydrophobically modified polyelectrolytes and photosensitive surfactants," Macromolecules 2004, 37:5397-5405.
Lee et al., "Solvent compatibility of poly(dimethylsiloxane)-based microfluidic devices," *Anal Chem* 2003, 75(23):6544-6554.
Leptihn et al., "In Vitro Reconstitution of Eukaryotic Ion Channels using Droplet Interface Bilayers," J Am Chem Soc 2011, 133:9370-9375.
Liu & Qin, "Functional control of cold- and menthol-sensitive TRPM8 ion channels by phosphatidylinositol 4,5-bisphosphate," *J Neurosci* 2005, 25:1674-1681.
Long et al., "Atomic structure of a voltage-dependent K+ channel in a lipid membrane-like environment," Nature 2007, 450:376-382.
Lu et al., "Biophysical aspects of agar-gel supported bilayer lipid membranes: a new method for forming and studying planar bilayer lipid membranes," *Bioelectrochem Bioenergetics* 1996, 39:285-289.
Lustig et al., "Solute Diffusion in Swollen Membranes .9. Scaling Laws for Solute Diffusion in Gels," *J Appl Polymer Sci* 1988, 36(4):735-747.
Malmstadt et al., "Automated formation of lipid-bilayer membranes in a microfluidic device," *Nano Letters* 2006, 6:1961-1965.
Malmstadt et al., "Long-Lived Planar Lipid Bilayer Membranes Anchored to an in Situ Polymerized Hydrogel," *Adv Mater* 2008, 20(1):84-89.
Malmstadt et al., "New approaches to lipid bilayer fabrication: microfluidic solvent extraction and hydrogel encapsulation," Adv Sci Technol 2006, 53:22-31.
Martens et al., "Tailoring the degradation of hydrogels formed from multivinyl poly(ethylene glycol) and poly(vinyl alcohol)macromers for cartilage tissue engineering," *Biomacromolecules* 2003, 4:283-292.
Matthews et al., "Design and fabrication of a micromachined planar patch-clamp substrate with integrated microfluidics for single-cell measurements," *J MEMS* 2006, 15: 214-222.
Mayer et al., "Microfabricated teflon membranes for low-noise recordings of ion channels in planar lipid bilayers," *Biophys J* 2003, 85:2684-2695.
Mayer et al., "Using ion channel-forming peptides to quantify protein-ligand interactions," J Am Chem Soc 2008, 130:1453-1465.
Maynard et al., "Thermoresponsive biohybrid materials synthesized by ATRP," J Mater Chem 2007, 17:4015-4017.
McDonald et al., "Poly(dimethylsiloxane) as a material for fabricating microfluidic devices," Acct Chem Res 2002, 35(7):491-499.
McKemy et al., "Identification of a cold receptor reveals a general role for TRP channels in thermosensation," *Nature* 2002, 416:52-58.
Meller et al., "Rapid nanopore discrimination between single polynucleotide molecules," *Proc Natl Acad Sci* 2000, 97:1079-1084.
Miller, "Ion Channel Reconstitution." Plenum Press, New York 1986.
Molokanova et al., "Bright future of optical assays for ion channel drug discovery," *Drug Discovery Today* 2008, 13:14-22.
Montal et al., "Formation of Bimolecular Membranes from Lipid Monolayers and a Study of Their Electrical Properties," *Proc Natl Acad Sci* 1972, 69(12):3561-3566.
Moscho et al., "Rapid preparation of giant unilamellar vesicles," Proc Natl Acad Sci 1996, 93:11443-11447.

(56) References Cited

OTHER PUBLICATIONS

Mueller et al., "Reconstitution of cell membrane structure in vitro and its transformation into an excitable system," *Nature* 1962, 194:979-980.
Nakane et al., "Nanopore sensors for nucleic acid analysis," J Phys Condensed Matter 2003, 15(32):R1365-R1393.
Naumowicz et al., "Impedance analysis of phosphatidylcholine membranes modified with gramicidin D," *Bioelectrochem* 2003, 61:21-27.
Nilius, "TRP channels in disease," Biochimica Et Biophysica Acta-Molecular Basis of Disease 2007, 1772:805-812.
Ottova & Tien, "Self-assembled bilayer lipid membranes: from mimicking biomembranes to practical applications," Bioelectrochem Bioenergetics 1997, 42:141-152.
Peier et al., "A TRP Channel that Senses Cold Stimuli and Menthol," Cell 2002, 108:705-715.
Perez et al., "Reconstitution of Expressed K—Ca Channels from *Xenopus*-Oocytes to Lipid Bilayers," Biophys J 1994, 66:1022-1027.
Portonovo & Schmidt, "Masking apertures enabling automation and solution exchange in sessile droplet lipid bilayers," *Biomed Microdevices* 2011, 14:187-191.
Poulos et al., "Automatable production of shippable bilayer chips by pin tool deposition for an ion channel measurement platform," *Biotechnol J* 2010, 5:511-514.
Poulos et al., "Automatable lipid bilayer formation and ion channel measurement using sessile droplets," *J Phys: Condens Matter* 2010, 22:454105.
Poulos et al., "Automatable lipid bilayer formation for ion channel studies," SPIE Proceedings 2008, 7035 (6 pages).
Poulos et al., "Electrowetting on dielectric-based microfluidics for integrated lipid bilayer formation and measurement," *Appl Phys Lett* 2009, 95 (3 pages).
Poulos et al., "Ion channel and toxin measurement using a high throughput lipid membrane platform," *Biosens Bioelectron* 2009, 24:1806-1810.
Purnell et al., "Nucleotide Identification and Orientation Discrimination of DNA Homopolymers Immobilized in a Protein Nanopore," NanoLetters 2008, 8(9):3029-3034.
Rehak et al., "Examination of bilayer lipid membranes for 'pin-hole' character," *The Analyst* 2004, 129:1014-1025.
Roháss et al., "PI(4,5)P2 regulates the activation and desensitization of TRPM8 channels through the TRP domain," Nat Neurosci 2005, 8:626-634.
Rosenbaum et al., "Subunit modification and association in VR1 ion channels," *BMC Neurosci* 2002, 3:4-13.
Sakmann & Neher (eds.), "Single-channel recording," Plenum Press, New York 1995.
Sakmann & Neher, "Patch clamp techniques for studying ionic channels in excitable membranes," Ann Rev Physiol 1984, 46:455-472.
Sandison et al., "Air-exposure technique for the formation of artificial lipid bilayers in microsystems," *Langmuir* 2007, 23:8277-8284.
Sandison et al., "Micromachined glass apertures for artificial lipid bilayer formation in a microfluidic system," *J Micromech Microeng* 2007, 17:S189-S196.
Sandison et al., "Rapid fabrication of polymer microfluidic systems for the production of artificial lipid bilayers," *J. Micromech Microeng* 2005, 15: S139-S144.
Schein et al., "Reconstitution in planar lipid bilayers of a voltage-dependent anion-selective channel obtained from paramecium mitochondria," *J Membrane Biol* 1976, 30(1):99-120.
Schindler & Quast, "Functional acetylcholine receptor from *Torpedo marmorata* in planar membranes," *Proc Natl Acad Sci* 1980, 77(5):3052-3056.
Schindler & Rosenbusch, "Matrix Protein from *Escherichia coli* Outer Membranes Forms Voltage-Controlled Channels in Lipid Bilayers," Proc Natl Acad Sci 1978, 75(8):3751-3755.
Schindler, "Formation of Planar Bilayers from Artificial or Native Membrane-Vesicles," FEBS Lett 1980, 122:77-79.

Schmalhofer et al., "A Pharmacologically Validated, High-Capacity, Functional Thallium Flux Assay for the Human Ether-à-go-go Related Gene Potassium Channel," Assay Drug Dev Technol 2010, 8(6):714-726.
Shim et al., "Stochastic Sensing on a Modular Chip Containing a Single Ion Channel," *Anal Chem* 2007, 79(6):2207-2213.
Sia et al., "Microfluidic devices fabricated in poly(dimethylsiloxane) for biological studies," *Electrophoresis* 2003, 24(21):3563-3576.
Sinner et al., "Functional tethered membranes," Curr Opinion Chem Biol 2001, 5(6):705-711.
Song et al., "Millisecond kinetics on a microfluidic chip using nanoliters of reagents," *J Am Chem Soc* 2003, 125(47):14613-14619.
Song et al., "Structure of staphylococcal alpha-hemolysin, a heptameric transmembrane pore," *Science* 1996, 274(5294):1859-66.
Suarezisla et al., "Single-Channel Recordings from Purified Acetylcholine-Receptors Reconstituted in Bilayers Formed at the Tip of Patch Pipets," Biochemistry 1983, 22:2319-2323.
Suzuki et al., "Electrophysiological recordings of single ion channels in planar lipid bilayers using a polymethyl methacrylate microfluidic chip," Biosens Bioelectron 2007, 22:1111-1115.
Suzuki et al., "Highly reproducible method of planar lipid bilayer reconstitution in polymethyl methacrylate microfluidic chip," *Langmuir* 2006, 22: 1937-1942.
Suzuki et al., "Planar lipid bilayer reconstitution with a microfluidic system," Lab Chip 2004, 4:502-505.
Syeda et al., "Screening Blockers Against a Potassium Channel with a Droplet Interface Bilayer Array," J Am Chem Soc 2008, 130:15543-15548.
Takagi et al., "A new method for the formation of bilayer membranes in aqueous solutions," Ann Rep Biol Fac Sci Osaka 1965, 13:107-110.
Tao & MacKinnon, "Functional analysis of Kv1.2 and paddle chimera Kv channels in planar lipid bilayers," *J Mol Biol* 2008, 382:24-33.
Terrettaz et al., "Highly Electrically Insulating Tethered Lipid Bilayers for Probing the Function of Ion Channel Proteins," *Langmuir* 2003, 19:5567-5569.
Thapliyal et al., "Automated lipid bilayer and ion channel measurement platform," Biosens Bioelectron 2011, 26:2651-2654.
Thorsen et al. "Microfluidic large-scale integration," *Science* (2002) 298, 580.
Thorsen et al., "Dynamic pattern formation in a vesicle-generating microfluidic device," *Phys Rev Lett* 2001, 86(18):4163-4166.
Titus et al., "A new homogeneous high-throughput screening assay for profiling compound activity on the human ether-a-go-go-related gene channel," *Analyt Biochem* 2009, 394(1):30-38.
Trenor et al., "Photoreversible Chain Extension of Poly(ethylene glycol)," Macromolec Chem Phys 2004, 205(6):715-723.
Tsavaler et al., "Trp-p8, a novel prostate-specific gene, is up-regulated in prostate cancer and other malignancies and shares high homology with transient receptor potential calcium channel proteins," *Cancer Res* 2001, 61:3760-3769.
Tsofina et al., "Production of Bimolecular Protein-Lipid Membranes in Aqueous Solution," Nature 1966, 212:681-683.
Unger et al., "Monolithic microfabricated valves and pumps by multilayer soft lithography," *Science* 2000, 288(5463), 113-116.
Vodyanoy et al., "Alamethicin-Induced Current-Voltage Curve Asymmetry in Lipid Bilayers," *Biophys J* 1983, 42:71-82.
Wang et al., "Development of a novel solid-phase extraction element for thermal desorption gas chromatography analysis," *J Chrom A* 2004, 1035(2):277-279.
Weigl et al., "Lab-on-a-chip for drug development," Adv Drug Delivery 2003, 55:349-377.
White, "The physical nature of planar bilayer membranes," in *Ion Channel Reconstitution*, Plenum Press, New York 1986, pp. 3-35.
Wonderlin et al., "Optimizing Planar Lipid Bilayer Single-Channel Recordings for High-Resolution with Rapid Voltage Steps," *Biophys J* 1990, 58:289-297.
Wong et al., "Single molecule measurements of channel proteins incorporated into biomimetic polymer membranes," Nanotechnology 2006, 17:3710-3717.

(56) References Cited

OTHER PUBLICATIONS

Wulff et al., "Voltage-gated potassium channels as therapeutic targets," Nat Rev Drug Discov 2009, 8(12):982-1001.
Yuan et al., "Bilayer Thickness Modulates the Conductance of the BK Channel in Model Membranes," Biophys J 2004, 86(6):3620-3633.
Zagnoni et al., "Bilayer lipid membranes from falling droplets," Anal Bioanal Chem 2009, 393:1601-1605.
Zagnoni et al., "Microfluidic array platform for simultaneous lipid bilayer membrane formation," Biosens Bioelectron 2009, 24:1235-1240.
Zakharian et al., "Gating of Transient Receptor Potential Melastatin 8 (TRPM8) Channels Activated by Cold and Chemical Agonists in Planar Lipid Bilayers," *J Neurosci* 2010, 30:12526-12534.
Zakharian et al., "Inorganic polyphosphate modulates TRPM8 channels," *PLoS One* 2009, 4 (12 pages).
Zhang & Barritt, "TRPM8 in prostate cancer cells: a potential diagnostic and prognostic marker with a secretory function?" *Endocr Relat Cancer* 2006, 13:27-38.
Zheng et al., "Screening of protein crystallization conditions on a microfluidic chip using nanoliter-size droplets," *J Am Chem Soc* 2003, 125(37):11170-11171.
Zholos, "Pharmacology of transient receptor potential melastatin channels in the vasculature," Brit J Pharmacol 2010, 159:1559-1571.
Zhou et al., "Properties of Herg channels stably expressed in HEK 293 cells studied at physiological temperature," *Biophys J* 1998, 74(1):230-241.
Zou et al., "Single HERG delayed rectifier K+ channels expressed in *Xenopus* oocytes," *Am J Physiol-Heart Circ Physiol* 1997, 272(3):H1309-H1314.
Preliminary Amendment filed Apr. 11, 2008 for U.S. Appl. No. 12/083,410, filed Oct. 13, 2006 and later granted as U.S. Pat. No. 8,038,885 on Oct. 18, 2011 (Inventors—Jacob J. Schmidt et al.) (10 pages).
Requirement for Restriction/Election issued Oct. 4, 2010 for U.S. Appl. No. 12/083,410, filed Oct. 13, 2006 and later granted as U.S. Pat. No. 8,038,885 on Oct. 18, 2011 (Inventors—Jacob J. Schmidt et al.) (7 pages).
Response to Election/Restriction filed Nov. 10, 2010 for U.S. Appl. No. 12/083,410, filed Oct. 13, 2006 and later granted as U.S. Pat. No. 8,038,885 on Oct. 18, 2011 (Inventors—Jacob J. Schmidt et al.) (9 pages).
Non-Final Rejection issued Nov. 18, 2010 for U.S. Appl. No. 12/083,410, filed Oct. 13, 2006 and later granted as U.S. Pat. No. 8,038,885 on Oct. 18, 2011 (Inventors—Jacob J. Schmidt et al.) (7 pages).
Response to Non-Final Rejection filed May 6, 2011 for U.S. Appl. No. 12/083,410, filed Oct. 13, 2006 and later granted as U.S. Pat. No. 8,038,885 on Oct. 18, 2011 (Inventors—Jacob J. Schmidt et al.) (13 pages).
Notice of Allowance issued Jun. 2011 for U.S. Appl. No. 12/083,410, filed Oct. 13, 2006 and later granted as U.S. Pat. No. 8,038,885 on Oct. 18, 2011 (Inventors—Jacob J. Schmidt et al.) (13 pages).
Non-Final Rejection issued Nov. 1, 2013 for U.S. Appl. No. 13/269,433, filed Oct. 7, 2011 (Inventors—Jacob J. Schmidt et al.) (8 pages).
Applicant Initiated Interview Summary (PTOL-413) issued on Nov. 20, 2013 for U.S. Appl. No. 13/269,433, filed Oct. 7, 2011 (Inventors—Jacob J. Schmidt et al.) (3 pages).
Preliminary Amendment filed Nov. 19, 2010 for U.S. Appl. No. 12/993,713, filed Feb. 1, 2011 (Inventors—Jacob J. Schmidt et al.) (8 pages).
Non-Final Rejection issued Jul. 8, 2013 for U.S. Appl. No. 12/993,713, filed Feb. 1, 2011 (Inventors—Jacob J. Schmidt et al.) (12 pages).
Applicant Initiated Interview Summary (PTOL-413) issued Sep. 26, 2013 for U.S. Appl. No. 12/993,713, filed Feb. 1, 2011 (Inventors—Jacob J. Schmidt et al.) (3 pages).

Amendment and Reponse to Office action filed Oct. 15, 2013 for U.S. Appl. No. 12/993,713, filed Feb. 1, 2011 (Inventors—Jacob J. Schmidt et al.) (10 pages).
Applicant Initiated Interview Summary (PTOL-413) issued Oct. 15, 2013 for U.S. Appl. No. 12/993,713, filed Feb. 1, 2011 (Inventors—Jacob J. Schmidt et al.) (3 pages).
Supplemental Amendment and Response to Office Action filed Nov. 8, 2013 for U.S. Appl. No. 12/993,713, filed Feb. 1, 2011 (Inventors—Jacob J. Schmidt et al.) (7 pages).
Notice of Allowance issued on Mar. 3, 2014 for U.S. Appl. No. 12/993,713, filed Feb. 1, 2011 (Inventors—Jacob J. Schmidt et al.) (8 pages).
International Search Report issued May 3, 2007 by the International Searching Authority for Application PCT/US2006/040200 filed Oct. 13, 2006, which published as WO 2007/047498 on Apr. 26, 2007 (Applicant—The Regents of the University of California // Inventors—Jacob J. Schmidt, et al.) (2 pages).
Written Opinion issued May 3, 2007 by the International Searching Authority for Application PCT/US2006/040200 filed Oct. 13, 2006, which published as WO 2007/047498 on Apr. 26, 2007 (Applicant —The Regents of the University of California // Inventors—Jacob J. Schmidt, et al.) (5 pages).
International Preliminary Report on Patentability issued Apr. 16, 2008 by the International Searching Authority for Application PCT/US2006/040200 filed Oct. 13, 2006, which published as WO 2007/047498 on Apr. 26, 2007 (Applicant—The Regents of the University of California // Inventors—Jacob J. Schmidt, et al.) (6 pages).
International Search Report issued Mar. 21, 2011 by the International Searching Authority for Application PCT/US2011/020284 filed Jan. 5, 2011, which published as WO 2011/085047 on Jul. 14, 2011 (Applicant—The Regents of the University of California // Inventors—Jason L. Poulos, et al.) (2 pages).
Written Opinion issued Mar. 21, 2011 by the International Searching Authority for Application PCT/US2011/020284 filed Jan. 5, 2011, which published as WO 2011/085047 on Jul. 14, 2011 (Applicant—The Regents of the University of California // Inventors—Jason L. Poulos, et al.) (8 pages).
International Preliminary Report on Patentability issued Jul. 10, 2012 by the International Bureau for Application PCT/US2011/020284 filed Jan. 5, 2011, which published as WO 2011/085047 on Jul. 14, 2011 (Applicant—The Regents of the University of California // Inventors—Jason L. Poulos, et al.) (9 pages).
International Search Report issued Oct. 26, 2009 by the International Searching Authority for Application PCT/US2009/044979 filed May 22, 2009, which published as WO 2009/143425 on Nov. 26, 2009 (Applicant—The Regents of the University of California // Inventors—Jacob J. Schmidt, et al.) (3 pages).
Written Opinion issued Oct. 26, 2009 by the International Searching Authority for Application PCT/US2009/044979 filed May 22, 2009, which published as WO 2009/143425 on Nov. 26, 2009 (Applicant—The Regents of the University of California // Inventors—Jacob J. Schmidt, et al.) (4 pages).
International Preliminary Report on Patentability issued Nov. 23, 2010 by the International Bureau for Application PCT/US2009/044979 filed May 22, 2009, which published as WO 2009/143425 on Nov. 26, 2009 (Applicant—The Regents of the University of California // Inventors—Jacob J. Schmidt, et al.) (5 pages).
Extended European Search Report issued on Apr. 23, 2013 for European Application No. 09751653.8, which is anational phase of PCT/US2009/044979, filed May 22, 2009 and later published as WO 2009/143425 on Nov. 26, 2009 (Applicant—The Regents of the University of California // Inventors—Jacob J. Schmidt, et al.) (8 pages).
Mueller et al, "Supramolecular Materials via Polymerization of Mesophases of Hydrated Amphiphiles", Chem. Rev. 2002, vol. 102, p. 727-757.
Zhan et al, "Hydrogel-Based Microreactors as a Functional Component of Microfluidic Systems", Analytical Chemistry, 2002, vol. 74, p. 4647-4652.
Non-Final Office Action issued Jan. 14, 2015 by the USPTO for U.S. Appl. No. 13/269,433, which was filed Oct. 7, 2011 and published as

(56) References Cited

OTHER PUBLICATIONS

US 2012-0025414 A1 on Feb. 2, 2012 (Applicant—The Regents of the University of California //1$^{st}$ Named Inventor — Schmidt//) (7 pages).
Alvarez O, et al. "How to set up a bilayer system. In Ion Channel Reconstitution." ed.; Miller, C., Ed. Plenum Press: New York, 1986: 115-139.
Cleveland PH, et al. "Nanoliter dispensing for uHTS using pin tools." Assay and Drug Development Technologies 2005, 3(2): 213-225.
Koper I. "Insulating tethered bilayer lipid membranes to study membrane proteins." Molecular BioSystems, 2007, 3: 651-657.
Krylov et al., "Water Permeability of Asymmetric Planar Lipid Bilayers—Leaflets of Different Composition Offer Independent and Additive Resistances to Permeation." JPG 2001, 118(4):333-340.
Mueller et al., "Reconstitution of excitable cell membrane structure in vitro," Circulation 1962, 26:1167-1171.
Rossi C and Chopineau J. Biomimetic tethered lipid membranes designed for membrane-protein interaction studies. Eur Biophys J 2007, 36(8): 955-965.
Strauss G and Hauser H. "Stabilization of lipid bilayer vesicles by sucrose during freezing." Proc Natl Acad Sci USA 1986, 83(8): 2422-2426.
Tanaka M and Sackmann E "Polymer-supported membranes as models of the cell surface". Nature, 2005, 437, 656-663.
White SH, et al. "Formation of planar bilayer membranes from lipid monolayers." Biophysical Journal 1976, 16: 481-489.
Examiner Interview Summary issued Jun. 16, 2011 for U.S. Appl. No. 12/083,410, filed Jun. 2, 2008 (Inventors—Schmidt, et al. //) (2 pages).
Examiner's Amendment issued Jun. 16, 2011 for U.S. Appl. No. 12/083,410, filed Jun. 2, 2008 (Inventors13 Schmidt, et al. //) (6 pages).
Petition for Review filed Aug. 1, 2011 for U.S. Appl. No. 12/083,410, filed Jun. 2, 2008 (Inventors—Schmidt, et al. //) (2 pages).
Notice of Allowance issued Aug. 4, 2011 for U.S. Appl. No. 12/083,410, filed Jun. 2, 2008 (Inventors—Schmidt, et al. //) (2 pages).
Petition Decision issued Sep. 1, 2011 for U.S. Appl. No. 12/083,410, filed Jun. 2, 2008 (Inventors—Schmidt, et al. //) (1 page).
Response to Non-Final Office Action filed Apr. 30, 2014 for U.S. Appl. No. 13/269,433, filed Oct. 7, 2011 (Inventors—Schmidt, et al. //) (11 pages).
Final Office Action issued Jun. 18, 2014 for U.S. Appl. No. 13/269,433, filed Oct. 7, 11 (Inventors—Schmidt, et al. //) (8 pages).
Response filed Oct. 7, 2013 for U.S. Appl. No. 12/993,713, filed May 22, 2009 (Inventors—Schmidt, et al. //) (10 pages).
Notice of Allowance issued Jun. 16, 2011 for U.S. Appl. No. 12/993,713, filed May 22, 2009 (Inventors—Schmidt, et al. //) (8 pages).
Preliminary Amendment filed Jun. 10, 2014 for U.S. Appl. No. 14/306,050, filed Jun. 16, 2014 (Inventors—Schmidt, et al. //) (10 pages).
Communication Pursuant to Rules 161(2) and 162 EPC issued Jan. 14, 2011 for European Application No. 09751653.8, which is a national phase of PCT/US2009/044979, filed May 22, 2009 and later published as WO 2009/143425 on Nov. 26, 2009 (Applicant—The Regents of the University of California // Inventors—Jacob J. Schmidt, et al.) (2 pages).
Communication Pursuant to Rules 161(2) and 162 EPC issued Aug. 14, 2012 for European Application No. 11732112.5, which is a national phase of PCT/US2011/020284, filed Jan. 5, 2011 and later published as WO 2011/085047 on Jul. 14, 2011 (Applicant—The Regents of the University of California // Inventors—Jason L. Poulos, et al.) (2 pages).
European Search Report issued Apr. 16, 2013 for European Patent Application EP 2521650 filed May 22, 2009 (Applicant—The Regents of the University of California // Inventors—Schmidt, et al.) (4 pages).
Voluntary Amendment filed Nov. 7, 2012 for European Application No. 12006905.9 filed on Oct. 5, 2012, which claims priority to U.S. Appl. No. 61/543,771 (Applicant—The Regents of the University of California // Inventors—Schmidt, et al.) (16 pages).
Voluntary Amendment filed Dec. 22, 2010 for European Application No. 09751653.8, which is a national phase of PCT/US2009/044979, filed May 22, 2009 and later published as WO 2009/143425 on Nov. 26, 2009 (Applicant—The Regents of the University of California // Inventors—Schmidt, et al.) (3 pages).
Portonovo, S.A. et al. (2013) "hERG Drug response measured in droplet bilayers." *Biomed. Microdevices* 15(2):255-259. (Abstract and Article attached).

\* cited by examiner

MASKING APERTURES ENABLING AUTOMATION AND SOLUTION EXCHANGE IN SESSILE BILAYERS

CROSS-REFERENCE TO RELATED APPLICATIONS

This Application claims the benefit of U.S. Provisional Application No. 61/543,771, filed on Oct. 5, 2011; which is incorporated herein by reference in its entirety.

STATEMENT REGARDING FEDERALLY SPONSORED RESEARCH

This invention was made with government support under 0644442, awarded by the National Science Foundation. The Government has certain rights in the invention.

BACKGROUND

Ion channels are present in every cell, playing key roles in a range of physiological processes, including cardiac and neural activity. Ion channel disorders have been implicated in epilepsy, cystic fibrosis, malaria, and a number of other diseases (Nilius, B. *Biochimica Et Biophysica Acta-Molecular Basis of Disease* 1772, 805-812 (2007). Because of their central importance, ion channels are intensely studied scientifically and are critical targets for drugs (Molokanova, M. et al. *Drug Discovery Today* 13, 14-22 (2008)) as well as the subject of safety concerns for off-target drug interactions (e.g., hERG cardiac $K^+$ channels) (Keating, M. T. et al. *Cell* 104, 569-580 (2001)).

Electrophysiological measurements of ion channels are complicated by the requirement that they must be incorporated into a lipid bilayer membrane to pass ionic current. These currents can be measured using the techniques of Patch Clamp (primarily used to measure ion channels in cells) or artificial lipid bilayers. Manual patch clamp is regarded as the gold standard for in vitro measurement of ion channels (Dunlop, J., et al., *Nature Reviews Drug Discovery* 7, 358-368 (2008); Hertzberg, R. P. et al. *Current Opinion in Chemical Biology* 4, 445-451 (2000), but despite its high quality data, patch clamp's low throughput and high equipment and skill requirements have limited its use to specialists. Ion channel drug screening in industry uses automated patch clamp (APC), an arrayed and automated version of manual patch clamp, which has increased measurement throughput, but is characterized by limited cell compatibility and very high instrumentation and consumable costs, also strongly limiting its use (Comley, J., *Drug Discovery World*, 47-57 (2003).

In vitro measurement of ion channels in artificial lipid bilayers is well-established for their isolation and study at the single molecule level (Wong, D., *Nanotechnology* 17, 3710-3717 (2006)) and uses electrical apparatus highly similar to patch clamp (Miller, C. Ion channel reconstitution. (Plenum Press, New York; 1986); Sakmann, B. & Neher, E. (eds.) Single-channel recording. (Plenum Press, New York; 1995)). Artificial bilayers are formed from constituent lipids and will reconstitute ion channels following addition of soluble channels or channel-containing vesicles to the surrounding membrane solution (Miller, C. Ion channel reconstitution. (Plenum Press, New York; 1986)). Ion channel measurement with cell-free artificial bilayers has a number of advantages over patch clamp including reduced equipment and training required and the ability to easily control the membrane composition and surrounding solution. Unfortunately, like patch clamp, it is a manual, low throughput measurement platform suited for specialists.

Electrophysiological activity of ion channels can be measured directly using cell-based patch clamp and cell-free artificial lipid bilayers. However, it is well recognized that these labor intensive platforms also require considerable technical expertise, severely limiting the potential user population as well as the scope and type of measurements that can be conducted. Studies of ion channels and transmembrane proteins in planar lipid bilayer membranes allow for functionality testing in highly controlled environments. Applications ranging from drug interaction testing to mutational studies have been demonstrated. Fully automatable formation and measurement of functional planar lipid bilayers have been shown using the contacting monolayer technique; automated formation of such 'droplet' lipid bilayers having consistent and repeatable sizes, however, has not been demonstrated. Further, the ability to perfuse such bilayers during measurement has not been shown.

Reconstitution of ion channels into artificial lipid bilayer membranes enables the isolation and study of individual channels as well as a high degree of control over the membrane composition and surrounding solution. Formation of artificial lipid bilayers from the contact of lipid monolayers self-assembled on oil/aqueous interfaces (Tsofina L M 1966) has been implemented in microfluidic devices (Funakoshi K 2006; Malmstadt 2006) and discrete droplet systems, (Holden M A 2007; Bayley H 2008; Poulos J L 2009) and has been the subject of much recent activity due to its compatibility with automated and parallel implementations (Poulos J L 2009; Poulos J L 2010; Thapliyal 2010) and capability to measure ion channels incorporated directly from primary cells or organelles (Leptihn S 2011).

It was previously shown that bilayer areas are highly sensitive to variations in positioning of the two aqueous phases (Heron A J 2007; Poulos J L 2010), which can in turn affect number of incorporated channels (Leptihn S 2011) and measurement noise (Wonderlin W F 1990; Mayer M 2003).

Thus, there exists a need for devices and methods for producing and measuring artificial bilayers. Such devices and methods are described herein.

SUMMARY OF THE INVENTION

In accordance with the purpose(s) of the invention, as embodied and broadly described herein, the invention, in one aspect, relates to devices and methods related to bilayer formation, such an amphiphilic molecule bilayer formation.

Disclosed herein is a device comprising: a) a first chamber; b) at least one second chamber; and c) a substrate defining at least one aperture having a diameter size, wherein the substrate is positioned between the at least one second chamber and the first chamber, and wherein the first chamber is in fluid communication with the at least one second chamber through the at least one aperture.

Also disclosed herein is a method of making a lipid bilayer comprising: a) providing a device comprising a substrate defining at least one aperture; b) providing an first solution on one side of the aperture; c) providing a second solution on the opposite side of the aperture from the first solution, wherein the first solution is immiscible in the second solution; d) providing a first amphiphilic molecule in the first solution, or second solution, or in both the first solution and second solution; e) contacting the first solution and the second solution through the aperture, thereby forming a first amphiphilic molecule monolayer; f) providing an fourth solution; g) providing a second amphiphilic molecule in the second solution, or fourth solution, or in both the second solution and fourth solution; h) submerging at least a portion of the fourth solution in the second solution, wherein the fourth solution is immiscible in the second solution, thereby forming a second amphiphilic molecule monolayer; and i) contacting the second amphiphilic molecule monolayer and the first amphiphilic molecule monolayer, thereby forming an amphiphilic molecule bilayer.

Also disclosed herein is a method of performing electrical measurements on an amphiphilic molecule bilayer comprising: a) providing an amphiphilic molecule bilayer formed at an aperture; and b) performing a measurement. In one aspect, providing an amphiphilic molecule bilayer comprises the methods for forming an amphiphilic molecule bilayer as described herein. For example, providing a lipid bilayer formed at an aperture can comprise: a) providing a device comprising a substrate defining at least one aperture; b) providing an first solution on one side of the aperture; c) providing a second solution on the opposite side of the aperture from the first solution, wherein the first solution is immiscible in the second solution; d) providing a first amphiphilic molecule in the first solution, or second solution, or in both the first solution and second solution; e) contacting the first solution and the second solution through the aperture, thereby forming a first amphiphilic molecule monolayer; f) providing an fourth solution; g) providing a second amphiphilic molecule in the second solution, or fourth solution, or in both the second solution and fourth solution; h) submerging at least a portion of the fourth solution in the second solution, wherein the fourth solution is immiscible in the second solution, thereby forming a second amphiphilic molecule monolayer; and i) contacting the second amphiphilic molecule monolayer and the first amphiphilic molecule monolayer, thereby forming an amphiphilic molecule bilayer.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 3) were averaged over 10 min and divided by the maximum current to obtain the fractional unblocked current, I/Imax. I/Imax (mean±SEM; n=3 (unless otherwise noted)) is plotted as a function of compound concentration and fitted as described in the text (solid lines). Experiments were conducted using proteoliposomes at a protein:lipid ratio of 1:1000 diluted to 1 mg/mL in reconstitution buffer with 2.5 mM PI(4,5)P2 added. (a) The $EC_{50}$ value of menthol was determined from the fit to be 111.8±2.4 mM, which compares well with previous work (D. Andersson, et al., *J. Neurosci.,* 2004, 24, 5364-5369; L. Zhang et al., *Endocr. Relat. Cancer,* 2006, 13, 27-38; I. Dragoni, et al., *J. Biol. Chem.,* 2006, 281, 37353-37360). (b) TRPM8 currents were initially evoked with the addition of 500 mM menthol, followed by the addition of varying concentrations of 2-APB. The $IC_{50}$ value for 2-APB was determined from the fit to be 4.9±0.2 mM, also comparing well with previous studies (H.-Z. Hu, et al., J. Biol. Chem., 2004, 279, 35741-35748.26, 46, 47; R. Eccles, J. Pharm. Pharmacol., 1994, 46, 618-630; A. Zholos, Br. J. Pharmacol., 2010, 159, 1559-1571).

FIG. 11A. Temperature-dependent activation of TRPM8. Measurements made in the presence of 2.5 µM PI(4,5)P$_2$ and in the absence of menthol. Single-channel temperature experiments began at 20° C. and the temperature then increased to 30° C. using an alcohol lamp (see Materials and Methods). $P_{open}$ increased 12-fold from 0.035±0.012 (n=7) to 0.410±0.035 (n=7) with a corresponding decrease in temperature from 30° C. (bottom panel) to 20° C. (top panel). FIG. 11B. Menthol-dependent activation of TRPM8. Measurements made in the presence of 2.5 µM PI(4,5)P$_2$ while the menthol concentration was varied. Temperature was kept constant at 20° C. Increasing the menthol concentration from 50 µM (bottom panel) to 500 µM (top panel), increased $P_{open}$ from 0.639±0.029 (n=9) to 0.967±0.013 (n=9).

Figure 1A:
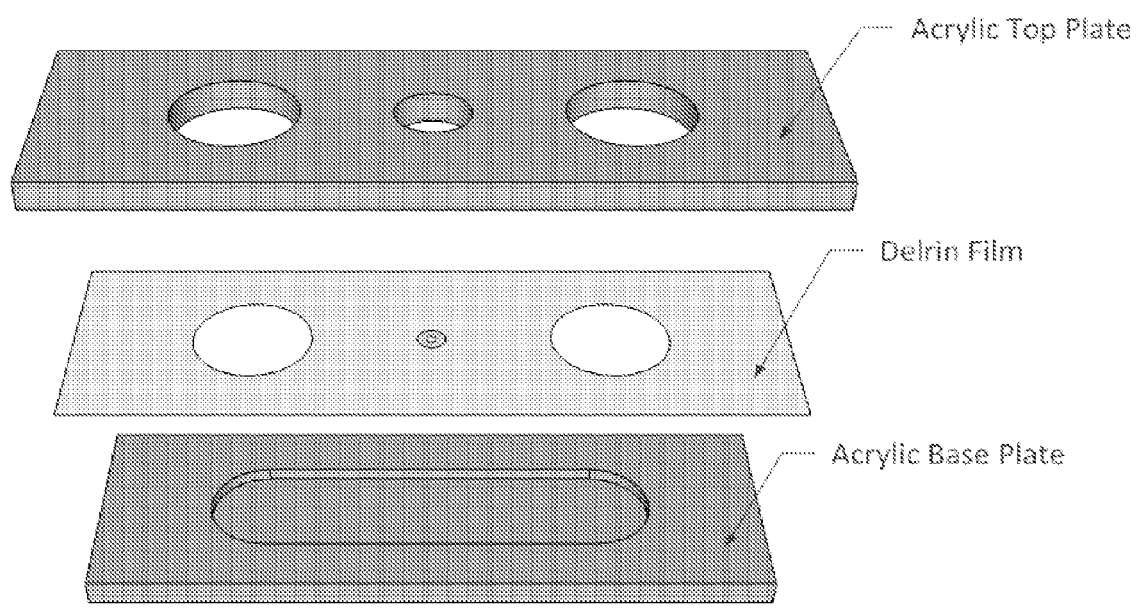
FIGS. 1A and 1B show diagrams of a bilayer measurement chamber. Top: Exploded view of top acrylic piece, center Delrin film containing cutouts for access to the lower fluidic channel and bilayer masking aperture and bottom acrylic piece connecting the side and center wells. Bottom: Cross-section of assembled chamber. Aqueous fluid is first loaded into one of the two side wells followed by loading of n-decane into the central well. The aperture size in the Delrin film masks the contact area between these two solutions. Lipids in the decane or aqueous solutions form a monolayer at this contact area. A Ag/AgCl pin electrode with sessile aqueous droplet in the central well causes self-assembly of another lipid monolayer; lowering the pin contacts the two monolayers to form a bilayer defined by the Delrin aperture. Electrical measurements of this bilayer are made by the pin electrode and Ag/AgCl counterelectrode inserted into the side well.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

1. Definitions

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

Disclosed are the components to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As used herein, the terms "optional" or "optionally" means that the subsequently described event or circumstance can or cannot occur, and that the description includes instances where said event or circumstance occurs and instances where it does not.

A used herein, the term "chemical agent" and the like terms refer to any natural or synthetic composition, molecule, or atom. For example, a chemical agent can be a drug that has been approved by the FDA. In another example, a chemical agent can be a molecule that is in clinical trial. Suitable chemical agents include, but are not limited to, substances, molecules, or atoms that targets membrane proteins such as ion channels and/or GPCRs or the membrane itself.

As used herein, the terms "effective amount" and "amount effective" refer to an amount that is sufficient to achieve the desired result or to have an effect on an undesired condition. For example, an effective amount of a chemical agent can achieve desired results in a formed amphiphilic bilayer.

As used herein, the term "derivative" refers to a compound having a structure derived from the structure of a parent compound (e.g., a compound disclosed herein, such as a lipid) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

(a) Amphiphilic Molecules

An "amphiphilic molecule" as used herein is a molecule composed of hydrophilic and hydrophobic groups. Amphiphilic molecules can form an amphiphilic bilayer under suitable conditions. An amphiphilic molecule can for an amphiphilic monolayer at the interface of an aqueous and non-aqueous solution. An amphiphilic molecule can be any amphiphilic molecule that forms a bilayer found in a mammalian cell. In one aspect, the amphiphilic molecule can be a lipid.

(i) Lipids

In one example, a lipid can comprise mixtures of two or more lipids. Suitable lipids can be generally classified as ionic (anionic/cationic/dipolar) and nonionic. More specifically, polymeric surfactants, silicon surfactants, fluorinated surfactants, oligomeric surfactants, dimeric surfactants, natural lipids, and the like, are suitable lipids for the devices and methods disclosed herein.

In one aspect, the lipids disclosed herein can comprise an anionic lipid. Any anionic lipid can be used. Suitable anionic lipids are commonly used in detergents, shampoos, soaps, etc., and can be obtained commercially or prepared by methods known in the art. They include, but are not limited to, alkylbenzene sulfonates (detergent), fatty acid based surfactants, lauryl sulfate (e.g., a foaming agent), di-alkyl sulfosuccinate (e.g., a wetting agent), lignosulfonates (e.g., a dispersant), and the like, including mixtures thereof. In other examples, linear alkylbenzene sulphonic acid, sodium lauryl ether sulphate, alpha olefin sulphonates, phosphate esters, sodium sulphosuccinates, hydrotropes, and the like, including mixtures thereof, can be used.

In another aspect, the lipids disclosed herein can comprise a cationic lipid. Any cationic lipid can be used. Suitable cationic lipids included, but are not limited to, quaternary ammonium compounds (e.g., tetraalkyl ammonium salts, pyridinium salts, imidazolinium salts, and the like). Such cationic lipids can be obtained commercially or can be prepared by methods known in the art.

In still another aspect, the lipids disclosed herein can comprise a nonionic lipid. Any nonionic lipid can be used. Suitable nonionic lipids do not ionize in aqueous solution, because their hydrophilic group is of a non-dissociable type, such as alcohol, phenol, ether, ester, or amide. They can be classified as ethers (e.g., polyhydric alcohols such as glycerin, solbitole, sucrose, etc.), fatty acid esters (e.g., glycerin fatty acid ester, sobitan fatty acid ester, sucrose fatty acid ester, etc.), esters (e.g., compounds made by applying, for example, ethylene oxide to a material having hydroxyl radicals such as high alcohol, alkyl-phenol, and the like), ether/esters (e.g., compounds made by applying, for example, the ethylene oxide to the fatty acid or polyhydric alcohol fatty acid ester, having both ester bond and ether bond in the molecule), and other types (e.g., the fatty acid alkanol-amide type or the alkylpolyglyceride type). Other suitable examples of nonionic lipids can include, but are not limited to, alcohol ethoxylates and alkyl phenol ethyoxylates, fatty amine oxides, alkanolamides, ethylene oxide/propylene oxide block copolymers, alkyl amine ethoxylates, tigercol lubricants, etc.

In yet another aspect, the lipids disclosed herein can comprise dipolar lipids. Any dipolar lipid can be used. Suitable dipolar lipids (called amphoteric or zwitterionic) exhibit both anionic and cationic dissociation. Suitable examples of dipolar lipids include, but are not limited to, products like betaines or sulfobetaines and natural substances such as amino acids and phospholipids. In one aspect, the betaines disclosed in U.S. Pat. Nos. 6,852,816; 6,846,795; 6,846,352; and 6,849,426, which are incorporated by reference in their entireties, can be used herein.

Other examples of suitable lipids include natural surfactants, which can have their source from plant or animal organs. In another example, a bolaform lipids can be used. A bolaform lipid is a lipid that has two hydrophilic head groups at opposite ends of a hydrophobic tail.

Mixtures of these lipids can also be used in the compositions and methods disclosed herein.

In one specific example, the disclosed lipids comprises diphytanoylphosphatidylcholine and/or 1,2-diphytanoyl-sn-glycero-3-phosphatidylcholine.

2. Devices

Disclosed herein is a device comprising: a) a first chamber; b) at least one second chamber; and c) a substrate defining at least one aperture having a diameter size, wherein the substrate is positioned between the at least one second chamber and the first chamber, and wherein the first chamber is in fluid communication with the at least one second chamber through the at least one aperture.

In one aspect, the substrate is a hydrophobic substrate. In one aspect, the hydrophobic substrate comprises polyoxymethylene, Teflon, polyethylene, acrylic resin, or a mixture thereof. For example, the hydrophobic substrate can be Delrin.

In one aspect, the substrate can be a film. In one aspect, the substrate can have a thickness that is less than 1 cm, 0.5 cm, or 0.1 cm. In another aspect the can have a thickness that is less than 500 μm, 200 μm, 100 μm, 50 μm, 25 μm, or 10 μm.

In one aspect, the first and at least one second chamber can be in any spatial orientation relative to one another. For example, the first and at least one second chamber can be side-by-side. In such example, the first chamber can be a first side chamber and the at least one second chamber can be at least one side second chamber. In another example, the first and at least one second chamber can above and below on another. In such example, the first chamber is a lower chamber and wherein the second chamber is at least one upper chamber.

In one aspect, the first chamber defines a first plate defining a solution chamber; and the second chamber defines a second plate defining at least one loading chamber having a diameter size. For example, the lower chamber defines a first plate defining a solution chamber; and the at least one upper chamber defines a second plate defining at least one loading chamber having a diameter size. In one aspect, the first plate and the second plate are made of a non-absorbing material. In one aspect, the first plate and the second plate are made of the same material. For expel, the first plate and the second plate can be acrylic based plates.

In one aspect, the substrate can be in contact with the first plate. In another aspect, the substrate can be in contact with the second plate. In another aspect, the substrate can be in contact with the first plate and the second plate.

In one aspect, the substrate can define the upper limit of the solution chamber. In another aspect, the substrate can define the lower limit of the at least one loading chamber.

In one aspect, the diameter of the at least one loading chamber is larger than the aperture of the substrate. In another aspect, the diameter of the at least one loading chamber is smaller than the solution chamber.

In one aspect, the first plate further defines at least one solution aperture and the substrate further defines at least one solution aperture, wherein the at least one solution aperture of the first plate is in fluid communication with the solution chamber through the at least one solution aperture of the substrate. For example, the first plate further defines at least one solution aperture and the hydrophobic substrate further defines at least one solution aperture, wherein the at least one solution aperture of the first plate is in fluid communication with the solution chamber through the at least one solution aperture of the hydrophobic substrate. In yet another aspect, the second plate further defines at least one solution aperture. The at least one solution aperture of the second plate can be in fluid communication with the at least one solution aperture of the first plate through the at least one solution aperture of the substrate. In one aspect, the device comprises at least two solution apertures. In another aspect, the device comprises at least four solution apertures. In another aspect, the device comprises at least six solution apertures.

In one aspect, the at least one solution aperture defines a solution inlet. In another aspect, the at least one solution aperture defines a solution outlet. In yet another aspect, the at least one solution aperture defines a solution inlet and a solution outlet. Means can be provided to produce a flow rate of a solution via the solution inlet and solution outlet. The solution can, for example, be a third solution as defined herein.

In one aspect, the diameter size of the at least one aperture is about 500 nm to about 10,000 μm. In another aspect, the diameter size of the at least one aperture is about 500 nm to about 5,000 μm. In yet another aspect, the diameter size of the at least one aperture is about 500 nm to about 1,000 μm. In yet another aspect, the diameter size of the at least one aperture is about 500 nm to about 750 μm. In yet another aspect, the diameter size of the at least one aperture is about 500 nm to about 500 µm. In yet another aspect, the diameter size of the at least one aperture is about 500 nm to about 200 µm. In yet another aspect, the diameter size of the at least one aperture is about 500 nm to about 100 µm. In yet another aspect, the diameter size of the at least one aperture is about 500 nm to about 50 µm. In yet another aspect, the diameter size of the at least one aperture is about 500 nm to about 20 µm. In yet another aspect, the diameter size of the at least one aperture is about 500 nm to about 10 µm. In yet another aspect, the diameter size of the at least one aperture is about 500 nm to about 5 µm. In yet another aspect, the diameter size of the at least one aperture is about 500 nm to about 1 µm. For example, the diameter size of the at least one aperture can be about 20 µm to about 500 µm. In another example, the diameter size of the at least one aperture is about 50 µm to about 200 µm.

In one aspect, the diameter size of the at least one aperture is smaller than the diameter size of the at least one loading chamber.

In one aspect, the thickness of the substrate and the diameter size of the aperture are such that an amphiphilic molecule bilayer, such as a lipid bilayer, can be formed. Generally, the thicker the substrate the larger the diameter size of the aperture has to be for the amphiphilic molecule bilayer, such as a lipid bilayer, to be formed.

In one aspect, the device further comprises means for performing a measurement. The measurement can be any measurement that produces information about the formation or disruption of an amphiphilic monolayer or amphiphilic bilayer. Such measurements are well known in the art. Suitable measurements include, but are not limited to, an electrical measurement, an optical measurement, a chemical measurement, an acoustic measurement, or combination thereof. The above measurements can include, fluorescence microscopy, dual polarization interferometery, x-ray diffraction, and electron microscopy. In one example, the measurement can be an electrical measurement. In one aspect, the means for performing electrical measurements comprises an electrode.

In one aspect, the first chamber further comprises a first fluid. In one aspect, the first fluid can be an aqueous fluid. An aqueous fluid can be water, such as deionized or milipure water. In another aspect, the first fluid can be a non-aqueous solution. In another aspect, the first fluid, such as an aqueous fluid, can comprise at least one amphiphilic molecule, such as a lipid. In one aspect, the first fluid can further comprise a chemical agent. In another aspect, the first fluid can further comprise a chemical agent and at least one amphiphilic molecule.

In one aspect, the at least one second chamber comprises a second fluid. In one aspect, the second fluid is immiscible in the first fluid. For example, the second fluid can be a non-aqueous solution. Suitable non-aqueous solutions are saturated hydrocarbon fluids such as n-hexane, n-heptane, n-octane, n-nonane, n-decane, and n-dodecane. Other suitable non-aqueous solutions include oils, such mineral oils. In another example, the second fluid can be an aqueous solution. In another example, the second fluid can be a non-aqueous solution and the first fluid can be an aqueous solution. In one aspect, viscosity of the second fluid and first fluids are substantially the same.

In one aspect, the second fluid comprises at least one amphiphilic molecule, such as at least one lipid. In one aspect, the first and second fluid comprises at least one amphiphilic molecule, such as at least one lipid. In another aspect, the second fluid comprises at least one amphiphilic molecule, such as at least one lipid and the first fluid does not comprise at least one amphiphilic molecule. In another aspect, the first fluid comprises at least one amphiphilic molecule, such as at least one lipid and the second fluid does not comprise at least one amphiphilic molecule.

In one aspect, the second fluid comprises a chemical agent. In another aspect, the second fluid comprises a chemical agent and at least on amphiphilic molecule, such a lipid.

In one aspect, the at least one second chamber is an array of loading chambers. The array can comprise at least 2, 3, 4, 5, 6, 7, 8, 9, 10, 15, 20, 30, 50, 100, 500 or 1000 loading chambers.

In one aspect, the at least one aperture is an array of apertures. The array can comprise at least 2, 3, 4, 5, 6, 7, 8, 9, 10, 15, 20, 30, 50, 100, 500 or 1000 apertures.

In one aspect, the at least one solution aperture can be an array of solution apertures. The array can comprise at least 2, 3, 4, 5, 6, 7, 8, 9, 10, 15, 20, 30, 50, 100, 500, 1000 or 2000 solution apertures.

In one aspect, the solution chamber comprises a third fluid. In one aspect, the third fluid and first fluid are identical. In another aspect, the third solution is immiscible in the second fluid. In another aspect, the third fluid comprises a chemical agent. In one aspect, the third fluid and first fluid are identical but for that the third fluid comprises a chemical agent which the first fluid does not. In one aspect, the third fluid is an aqueous solution. In another aspect, the third fluid is a non-aqueous solution. In one aspect, the device comprises means for flowing a third fluid through the solution chamber. In one aspect, the means for flowing a third fluid through the solution chamber comprises a fluid inlet and a fluid outlet.

In one aspect, the chemical agent comprises a chemical agent that interacts with membrane proteins, receptors, or ion channels. In another aspect, the chemical agent comprises a chemical agent that modifies membrane proteins, receptors, or ion channels. In another aspect, the chemical agent comprises a chemical agent that disrupts membrane proteins, receptors, or ion channels. In another aspect, the chemical agent comprises a chemical agent that does not interact with membrane proteins, receptors, or ion channels.

In one aspect, the first chamber or at least one second chamber comprises a fourth solution. For example, the at least one second chamber can comprise the fourth solution. In another example, the first chamber can comprise the fourth solution. In one aspect, when the at least one second chamber comprises a second solution the fourth solution is immiscible in the second solution. In one aspect, the further solution is immiscible in a fluid present in the first chamber or the at least one second chamber. In another aspect, when the first chamber comprises a first solution the fourth solution is immiscible in the first solution. In one aspect, the fourth solution is an aqueous solution. In another aspect, the fourth solution is a non-aqueous solution. In one aspect, the fourth solution comprises at least one amphiphilic molecule, such as a lipid. In another aspect, the fourth solution comprises a chemical agent. In one aspect, the fourth solution is a droplet, such as an aqueous droplet. For example, the loading chamber comprises an aqueous droplet. In one aspect, least a portion of the fourth solution is in contact with means for performing measurements, such as electrical measurements. For example, the loading chamber can comprise an aqueous droplet, and wherein at least a portion of the aqueous droplet is in contact with the means for performing electrical measurements.

3. Methods (a) Method of Making Bilayers

Also disclosed herein is a method of making a lipid bilayer comprising: a) providing a device comprising a substrate defining at least one aperture; b) providing an first solution on one side of the aperture; c) providing a second solution on the opposite side of the aperture from the first solution, wherein the first solution is immiscible in the second solution; d) providing a first amphiphilic molecule in the first solution, or second solution, or in both the first solution and second solution; e) contacting the first solution and the second solution through the aperture, thereby forming a first amphiphilic molecule monolayer; f) providing an fourth solution; g) providing a second amphiphilic molecule in the second solution, or fourth solution, or in both the second solution and fourth solution; h) submerging at least a portion of the fourth solution in the second solution, wherein the fourth solution is immiscible in the second solution, thereby forming a second amphiphilic molecule monolayer; and i) contacting the second amphiphilic molecule monolayer and the first amphiphilic molecule monolayer, thereby forming an amphiphilic molecule bilayer.

In one aspect, the device is a device disclosed herein.

In one aspect, the fourth solution is a droplet.

In another aspect, the fourth solution comprises an amphiphilic molecule. For example, the fourth solution can comprise a lipid.

In one aspect, the amphiphilic molecule bilayer is a lipid bilayer. In one aspect, the amphiphilic molecule bilayer comprises at least one ion channel. In another aspect, the amphiphilic molecule bilayer comprises at least one receptor. In another aspect, the amphiphilic molecule bilayer comprises at least one membrane proteins. In another aspect, the amphiphilic molecule bilayer comprises at least one ion channel and at least one receptor. In another aspect, the amphiphilic molecule bilayer comprises at least one ion channel, at least one receptor, and at least one membrane protein.

In one aspect, the amphiphilic molecule bilayer is stable for at least 3 days, 5 days, 1 week, 2 weeks, 1 month, 3 months or 6 months.

In one aspect, the method further comprises providing means for performing measurements. Suitable means for performing measurements are known in the art and include, but are not limited to means for performing electrical measurements, means for performing optical measurements, means for performing chemical measurements, means for performing acoustic measurements, or a combination thereof. For example, the method can further comprise providing means for performing electrical measurements.

In one aspect, the method further comprises performing measurements. Suitable measurements are known in the art and include, but are not limited to an electrical measurement, an optical measurement, a chemical measurement, an acoustic measurement, or combination thereof. For example, the method can further comprise performing an electrical measurement.

In one aspect, at least a portion of the fourth solution is in contact with the means for performing measurements, such as electrical measurements. For example, at least a portion of the droplet is in contact with the means for performing measurements, such as electrical measurements.

In one aspect, the method further comprises providing a third solution on the same side of the aperture as the first solution. In one aspect, the third solution is identical to the first solution. In another aspect, the third solution is an aqueous solution. In another aspect, the third solution is a non-aqueous solution. In one aspect, the chemical agent in the third solution can be present before or after the formation of the amphiphilic molecule bilayer. For example, the chemical agent in the third solution can be present before the formation of the amphiphilic molecule bilayer. In another example, the chemical agent in the third solution can be present after the formation of the amphiphilic molecule bilayer. In another example, the third solution does not comprise a chemical agent before the formation of the amphiphilic molecule bilayer.

In one aspect, the third solution has a flow rate. The flow rate can be at least 1 ml/hr, 3 ml/hr, 5, ml/hr, 10 ml/hr, 15 ml/hr, 20 ml/hr, 25 ml/hr, 30 ml/hr or 50 ml/hr. In one aspect, the flow rate of the third solution does not influence the stability of the amphiphilic molecule bilayer.

In one aspect, the third solution further comprises a chemical agent.

In one aspect, the first solution is an aqueous solution. In another aspect, the first solution is a non-aqueous solution. In one aspect, the first solution further comprises a chemical agent. For example, the chemical agent in the first solution can be present before the formation of the amphiphilic molecule bilayer. In another example, the chemical agent in the first solution can be present after the formation of the amphiphilic molecule bilayer. In another example, the first solution does not comprise a chemical agent before the formation of the amphiphilic molecule bilayer.

In one aspect, the second solution is a non-aqueous solution. In another aspect, the second solution is an aqueous solution. In one aspect, the second solution further comprises a chemical agent. For example, the chemical agent in the second solution can be present before the formation of the amphiphilic molecule bilayer. In another example, the chemical agent in the second solution can be present after the formation of the amphiphilic molecule bilayer. In another example, the second solution does not comprise a chemical agent before the formation of the amphiphilic molecule bilayer.

In one aspect, the chemical agent comprises a chemical agent that interacts with membrane proteins, receptors, or ion channels. In another aspect, the chemical agent comprises a chemical agent that modifies membrane proteins, receptors, or ion channels. In another aspect, the chemical agent comprises a chemical agent that disrupts membrane proteins, receptors, or ion channels. In another aspect, the chemical agent comprises a chemical agent that does not interact with membrane proteins, receptors, or ion channels. In a further aspect the chemical agent is known to interact with amphiphilic molecule bilayer.

In one aspect, the defining at least one aperture is an array of apertures. The array can comprise at least 2, 3, 4, 5, 6, 7, 8, 9, 10, 15, 20, 30, 50, 100, 500 or 1000 apertures.

In one aspect, a chemical agent can be added to the first solution, second solution, third solution or fourth solution before or after the formation of the amphiphilic molecule bilayer. For example, a chemical agent can be added to the first solution before or after the formation of the amphiphilic molecule bilayer. In another example, a chemical agent can be added to the second solution before or after the formation of the amphiphilic molecule bilayer. In another example, a chemical agent can be added to the third solution before or after the formation of the amphiphilic molecule bilayer. In another example, a chemical agent can be added to the fourth solution before or after the formation of the amphiphilic molecule bilayer.

(b) Methods of Performing Electrical Measurements on a Bilayer

Also disclosed herein is a method of performing electrical measurements on an amphiphilic molecule bilayer comprising: a) providing an amphiphilic molecule bilayer formed at an aperture; and b) performing a measurement.

In one aspect, providing an amphiphilic molecule bilayer comprises the methods for forming an amphiphilic molecule bilayer as described herein. For example, providing a lipid bilayer formed at an aperture can comprise: a) providing a device comprising a substrate defining at least one aperture; b) providing an first solution on one side of the aperture; c) providing a second solution on the opposite side of the aperture from the first solution, wherein the first solution is immiscible in the second solution; d) providing a first amphiphilic molecule in the first solution, or second solution, or in both the first solution and second solution; e) contacting the first solution and the second solution through the aperture, thereby forming a first amphiphilic molecule monolayer; f) providing an fourth solution; g) providing a second amphiphilic molecule in the second solution, or fourth solution, or in both the second solution and fourth solution; h) submerging at least a portion of the fourth solution in the second solution, wherein the fourth solution is immiscible in the second solution, thereby forming a second amphiphilic molecule monolayer; and i) contacting the second amphiphilic molecule monolayer and the first amphiphilic molecule monolayer, thereby forming an amphiphilic molecule bilayer.

In one aspect, the aperture can be an aperture as disclosed herein. In another aspect, the aperture can be present in a device disclosed herein. In one aspect, the aperture can be an array of apertures. The array can comprise at least 2, 3, 4, 5, 6, 7, 8, 9, 10, 15, 20, 30, 50, 100, 500 or 1000 apertures.

In one aspect, the device can be a device disclosed herein.

In one aspect, the amphiphilic molecule bilayer is a lipid bilayer. In one aspect, the amphiphilic molecule bilayer comprises at least one ion channel. In another aspect, the amphiphilic molecule bilayer comprises at least one receptor. In another aspect, the amphiphilic molecule bilayer comprises at least one membrane proteins. In another aspect, the amphiphilic molecule bilayer comprises at least one ion channel and at least one receptor. In another aspect, the amphiphilic molecule bilayer comprises at least one ion channel, at least one receptor, and at least one membrane protein.

In one aspect, the fourth solution is a droplet.

In one aspect, the method further comprises performing measurements prior to providing an amphiphilic molecule bilayer. In one aspect, the method further comprises performing measurements during the formation of an amphiphilic molecule bilayer.

In one aspect, the measurement can be an electrical measurement, an optical measurement, a chemical measurement, an acoustic measurement, or combination thereof. For example, the measurement can be an electrical measurement or an optical measurement. In another example, the measurement can be an electrical measurement.

In one aspect, performing a measurement comprises providing means for performing measurements. Suitable means for performing measurements are known in the art and include, but are not limited to means for performing electrical measurements, means for performing optical measurements, means for performing chemical measurements, means for performing acoustic measurements, or a combination thereof. For example, the method can further comprise providing means for performing electrical measurements.

In one aspect, performing electrical measurements comprises an electrode.

In one aspect, at least a portion of the fourth solution is in contact with at least a portion of the means for performing electrical measurements. In one aspect, the fourth solution can be a droplet. For example, at least portion of the droplet can be in contact with at least a portion of the electrode.

In one aspect, the method can further comprise detecting a change in the measurements. For example, the method can further comprise detecting a change in the electrical measurements or optical measurements. In another example, the method can further comprise detecting a change in the electrical measurements.

In one aspect, the method further comprises providing a third solution on the same side of the aperture as the first solution.

In one aspect, the method further comprises providing a third solution on the same side of the aperture as the first solution. In one aspect, the third solution is identical to the first solution. In another aspect, the third solution is an aqueous solution. In another aspect, the third solution is a non-aqueous solution. In one aspect, the chemical agent in the third solution can be present before or after the formation of the amphiphilic molecule bilayer. For example, the chemical agent in the third solution can be present before the formation of the amphiphilic molecule bilayer. In another example, the chemical agent in the third solution can be present after the formation of the amphiphilic molecule bilayer. In another example, the third solution does not comprise a chemical agent before the formation of the amphiphilic molecule bilayer.

In one aspect, the third solution has a flow rate. The flow rate can be at least 1 ml/hr, 3 ml/hr, 5, ml/hr, 10 ml/hr, 15 ml/hr, 20 ml/hr, 25 ml/hr, 30 ml/hr or 50 ml/hr. In one aspect, the flow rate of the third solution does not influence the stability of the amphiphilic molecule bilayer.

In one aspect, the third solution further comprises a chemical agent.

In one aspect, the first solution is an aqueous solution. In another aspect, the first solution is a non-aqueous solution. In one aspect, the first solution further comprises a chemical agent. For example, the chemical agent in the first solution can be present before the formation of the amphiphilic molecule bilayer. In another example, the chemical agent in the first solution can be present after the formation of the amphiphilic molecule bilayer. In another example, the first solution does not comprise a chemical agent before the formation of the amphiphilic molecule bilayer.

In one aspect, the second solution is a non-aqueous solution. In another aspect, the second solution is an aqueous solution. In one aspect, the second solution further comprises a chemical agent. For example, the chemical agent in the second solution can be present before the formation of the amphiphilic molecule bilayer. In another example, the chemical agent in the second solution can be present after the formation of the amphiphilic molecule bilayer. In another example, the second solution does not comprise a chemical agent before the formation of the amphiphilic molecule bilayer.

In one aspect, the chemical agent comprises a chemical agent that interacts with membrane proteins, receptors, or ion channels. In another aspect, the chemical agent comprises a chemical agent that modifies membrane proteins, receptors, or ion channels. In another aspect, the chemical agent comprises a chemical agent that disrupts membrane proteins, receptors, or ion channels. In another aspect, the chemical agent comprises a chemical agent that does not interact with membrane proteins, receptors, or ion channels. In a further aspect, the chemical agent is known to interact with amphiphilic molecule bilayer.

In one aspect, a chemical agent can be added to the first solution, second solution, third solution or fourth solution before or after the formation of the amphiphilic molecule bilayer. For example, a chemical agent can be added to the first solution before or after the formation of the amphiphilic molecule bilayer. In another example, a chemical agent can be added to the second solution before or after the formation of the amphiphilic molecule bilayer. In another example, a chemical agent can be added to the third solution before or after the formation of the amphiphilic molecule bilayer. In another example, a chemical agent can be added to the fourth solution before or after the formation of the amphiphilic molecule bilayer.

In one aspect, the method provides information regarding the potency of the chemical agent. For example, the method provides information regarding the potency of the chemical agent towards an amphiphilic molecule bilayer.

In one aspect, the at least one second amphiphilic molecule is the at least one first amphiphilic molecule.

4. Examples

To address drawbacks in the prior art, an apparatus was designed for artificial lipid bilayer formation and measurement plate which constrains the contact area of the two aqueous phases, also constraining the bilayer area. The apparatus consists of a lower aqueous solution chamber plate, a hydrophobic film in which a small aperture is cut, and a top chamber plate that allows for top loading and electrical access of all solutions. Lipid bilayers are formed by contacting monolayers through the small aperture in the hydrophobic film, which constrains the bilayer size. The measurements in the examples demonstrate a reduced sensitivity of bilayer area to the relative position of the aqueous phases, reducing the precision needed by fluid handling and motion control hardware in automation. The apparatus is also easily arrayed and compatible with SBS standard instrumentation. The examples also demonstrate fully automated fluid exchange of the lower aqueous solution with intact droplet bilayers allowing for stable solution perfusion. While masking of lipid bilayers formed by contacting monolayers has been studied previously (Zagnoni M 2009), here were present a platform that is easily automatable and scalable, presenting a way forward toward high-throughput study.

5. Example 1

(a) Experimental Conditions (i) Bilayer Formation Apparatus

Chambers were made from 0.125" thick acrylic (McMaster-Carr) and 0.003" thick Delrin film (McMaster-Carr). Two acrylic pieces were milled to form fluidic wells and channels by stacking them vertically and sandwiching the Delrin. Apertures in the Delrin film were cut using a $CO_2$ laser (Universal Laser Systems) to connect the wells formed by the upper and lower acrylic pieces. Two wells were connected through a channel in the lower acrylic piece. Aperture sizes were measured microscopically. The center measurement well was connected to the channel through a pore between 50-200 µm in diameter laser cut into the Delrin film on which the bilayer is formed. A 0.0625" thick layer of PDMS elastomer (Sylgard, Dow Corning) cut with holes matching those in the acrylic pieces was placed on top of the Delrin film to form a sealing gasket. Once assembled, all pieces were clamped together (FIG. 1).

(ii) Lipid Bilayer Formation

Measurement buffer (MB) containing liposomes were made as previously described (Poulos J L 2010). Briefly, a 1 ml solution of 1M KCL, 10 mM Tris-HCL (Sigma), pH 8.0, and additionally containing 33 mg of 1,2-Diphytanoyl-sn-Glycero-3-Phosphocholine (DPhPC) lipid (Avanti Polar Lipids), was extruded through a 200 nm filter (Avanti). 150 µl MB was first loaded into the aqueous inlet to completely fill the portion of the chamber below the Delrin film. Next, 40 µl of n-decane (MP Biomedicals) was loaded into the measurement well to fill the portion of the well directly above the pore in the Delrin film. This allows the liposome-containing aqueous solution below the film to come into contact with the n-decane within the Delrin pore, where a lipid monolayer self-assembles.

(iii) Electrode Fabrication

Silver pins were fabricated using 16 gauge silver wire (0.999 purity, C. C. Silver & Gold). The pins were cut to approximately 1 inch and electrical discharge machining was used to create a blunt end and cut slots 0.05" deep and 0.015" wide into the ends of the pins. Counter electrodes were made from 200 µm diameter silver wire (Ted Pella). The silver wires were chloridized by immersing them in bleach for approximately 1 min, followed by a deionized (DI) water rinse.

(iv) Bilayer Formation and Measurement

Figure 1B:
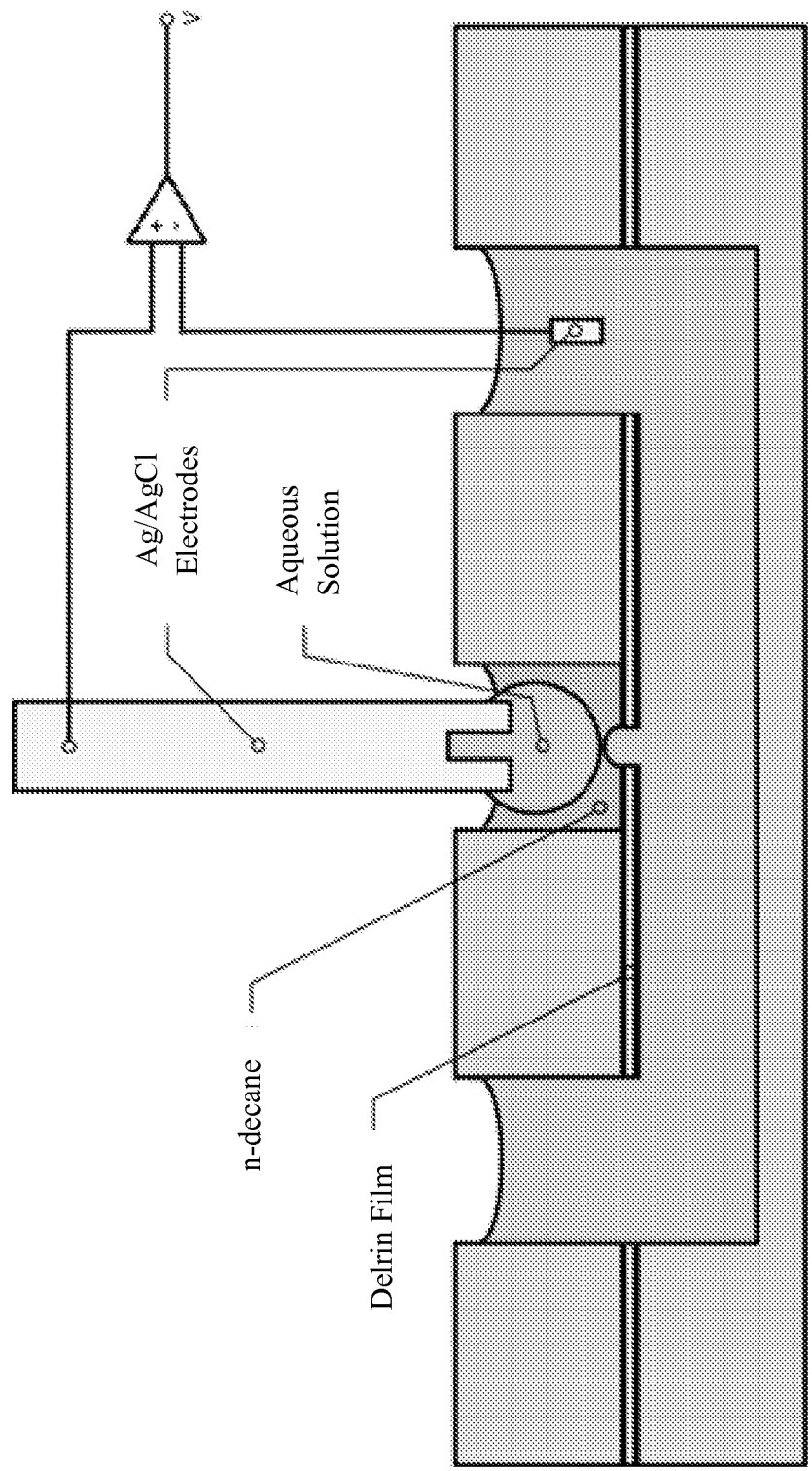

As described previously (Poulos J L 2010), the chloridized pin was lowered into liposome-containing MB to a depth of approximately 10 mm for 1 s and removed (FIG. 1(b)), resulting in a small ≈1.1 µl droplet hanging from the end of the pin. This pin with hanging droplet was then lowered into the decane solution. After waiting approximately 1 min. for lipid monolayer formation, the pin was lowered further using a micromanipulator (Newport) until the droplet contacted the lower aqueous phase within the Delrin pore, forming a lipid bilayer membrane.

For electrical measurement, the apparatus was placed inside a Faraday cage and the Ag/AgCl pin and counterelectrode were connected to an Axopatch 200B amplifier (Axon Instruments). The signals were digitized with a Digidata 1332A (Axon Instruments) at 5 kHz, filtered in hardware with a 1 kHz Bessel filter and subsequently filtered further with a 30 Hz Bessel filter and analyzed with Clampfit software (Axon Instruments).

In fluid exchange experiments, PTFE tubing (Zeus) was inserted into one of the inlet ports of the lower channel of the measurement chamber and connected to a syringe pump (KD Scientific) actuating a 10 mL glass syringe (Hamilton) filled with MB. After the lower aqueous chamber was filled, the measurement well was loaded with n-decane and bilayers formed after pin insertion as described above.

(b) Results

Best results for the laser cut apertures were obtained when the Delrin films were thinned by raster etching before cutting, which involves a laser burning away sections of material to reduce film thickness. For apertures 50 µm-200 µm in diameter, bilayer formation, measured capacitively, was observed to occur upon contact of the sessile droplet to the Delrin film, enduring stably at least several hours, as previously described (Poulos J L 2009; Poulos J L 2010). Measurements of ion channels in lipid bilayers formed using the masking apertures were indistinguishable from those made without the apertures (Data not shown.). Bilayer formation was highly repeatable, and droplets could easily be removed and replaced to subsequently form bilayers—in a repeatability experiment, 51 bilayers were formed in 51 attempts.

Bilayer areas without these masking apertures are highly sensitive to the relative positions of the droplets (Heron A J 2007; Poulos J L 2010). The influence of the apertures was explored on this effect. In one set of experiments, the pin was lowered to contact the droplet to the Delrin apertures until an increase in capacitance was measured, signifying bilayer formation. The pin was then further lowered in steps of 50 μm and the capacitance measured again. From these values the 30 pF background capacitance, measured with the pin approximately 1 mm away from the aperture, was subtracted and the resulting bilayer capacitance was plotted, shown in FIG. 2. The variation of measured capacitance with vertical pin position was markedly reduced with the Delrin apertures as compared to our previous measurements.

Figure 3:
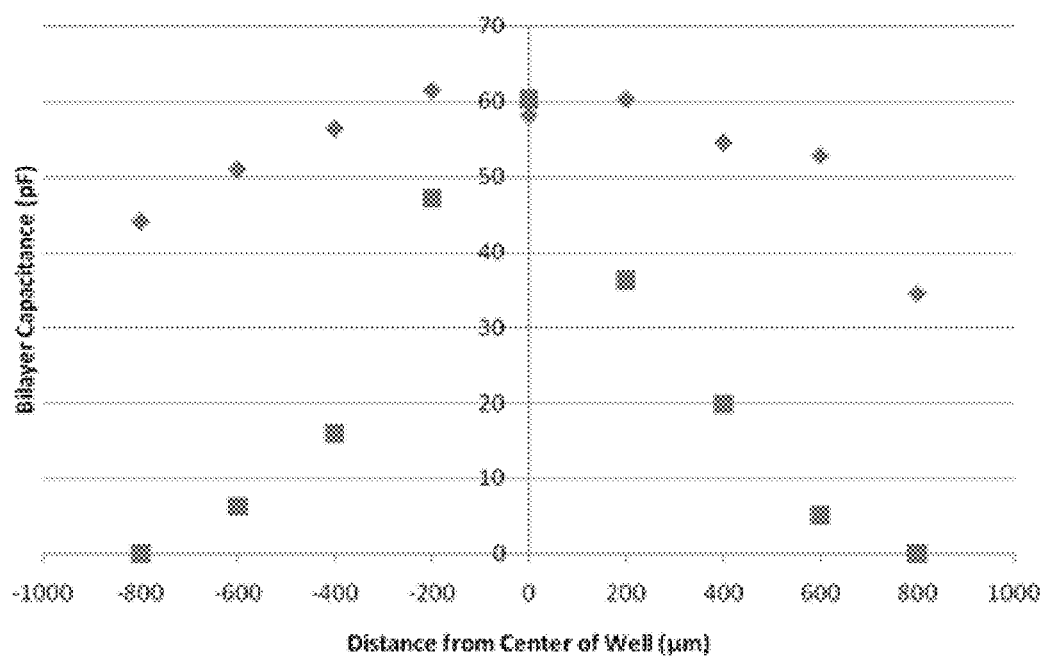
FIG. 3 shows the bilayer capacitance as a function of lateral pin position with a 150 µm diameter masking aperture (squares) and with no aperture (diamonds). For each measurement, the pin is raised vertically 500 µm from its starting position and moved laterally before being lowered.

The sensitivity of bilayer area was also investigated to the lateral position of the pin. A pin with 2 μl sessile droplet was axially aligned with the center of a 150 μm aperture and lowered to form a bilayer. After each capacitance measurement, the pin was raised and moved in 200 μm steps laterally before being lowered again, after which the capacitance was measured. These experiments were compared to measurements taken with no separating Delrin film. With the Delrin film, the bilayer capacitance was still within 90% of its original value when the droplet was positioned over 500 μm from the aperture center. In contrast, without the masking aperture, the bilayer capacitance decreased to approximately 15% of its original value (FIG. 3).

Figure 4:
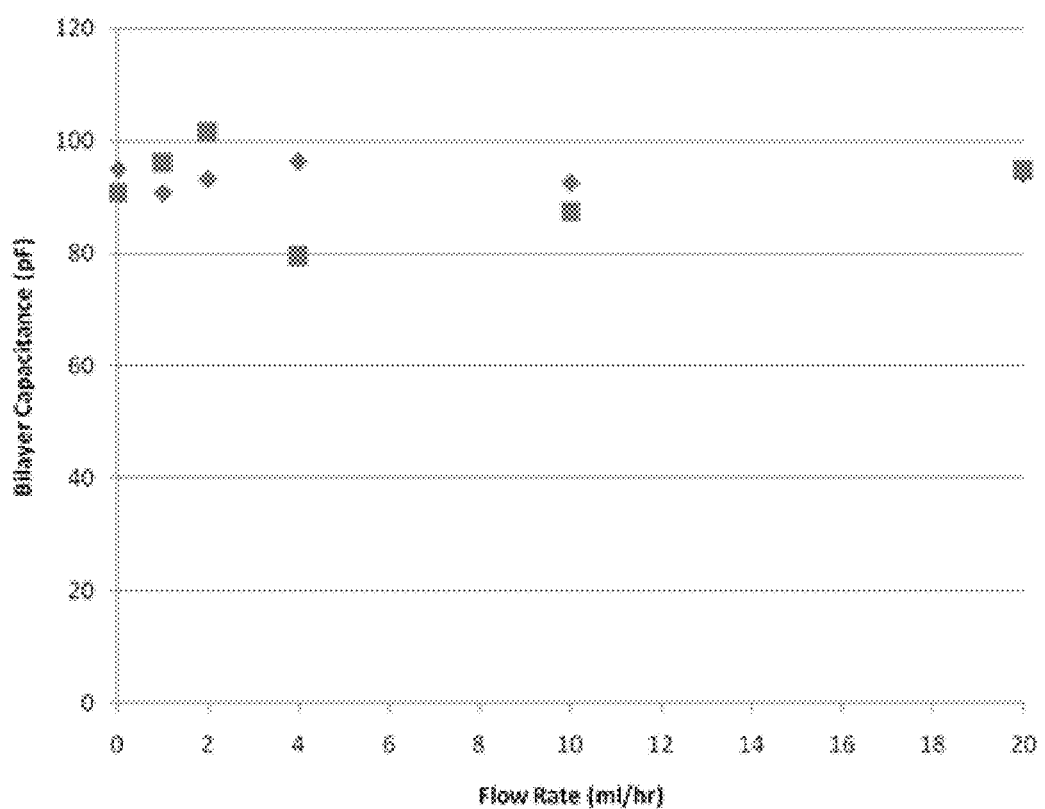
FIG. 4 show that masking apertures increase tolerance of bilayers to solution flow. Bilayer capacitance is measured as a function of flow rate of the buffer in the lower aqueous chamber. Data shown from two separate trials with a 200 µm diameter aperture. Without the masking aperture, bilayer failure was immediate even for flow rates <1 ml/hr.
Figure 5:
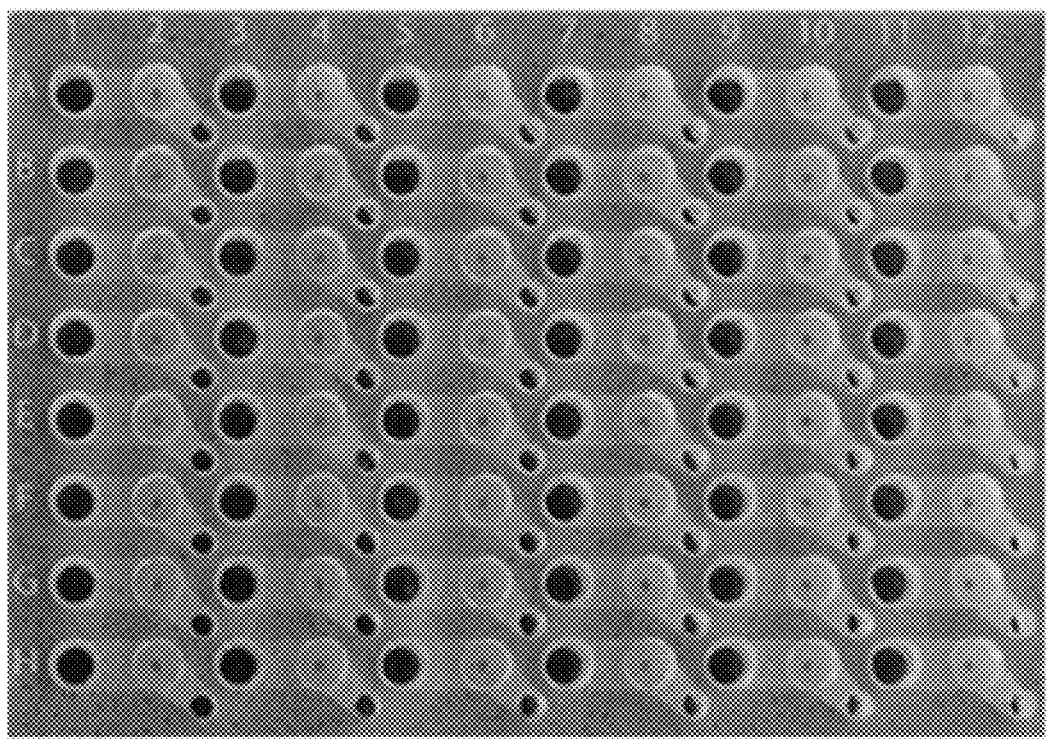
FIG. 5 show fabricated array plate of wells depicted in FIG. 1 of manuscript. Well spacing is SBS standard and compatible with multichannel fluid handling and motion control standard apparatus.

The effect of active solution exchange through the lower chamber was determined by measuring bilayer capacitance while fluid was pumped at different flow rates using a syringe pump. Lipid bilayers were formed using a 200 μm diameter aperture and measured in flow rates of 0-20 ml/hr. Data are shown in FIG. 4 from two experiments. Similar experiments without the masking aperture resulted in immediate bilayer failure as the lower aqueous solution would rise up through the measurement well, even at very low flow rates.

Figure 2:
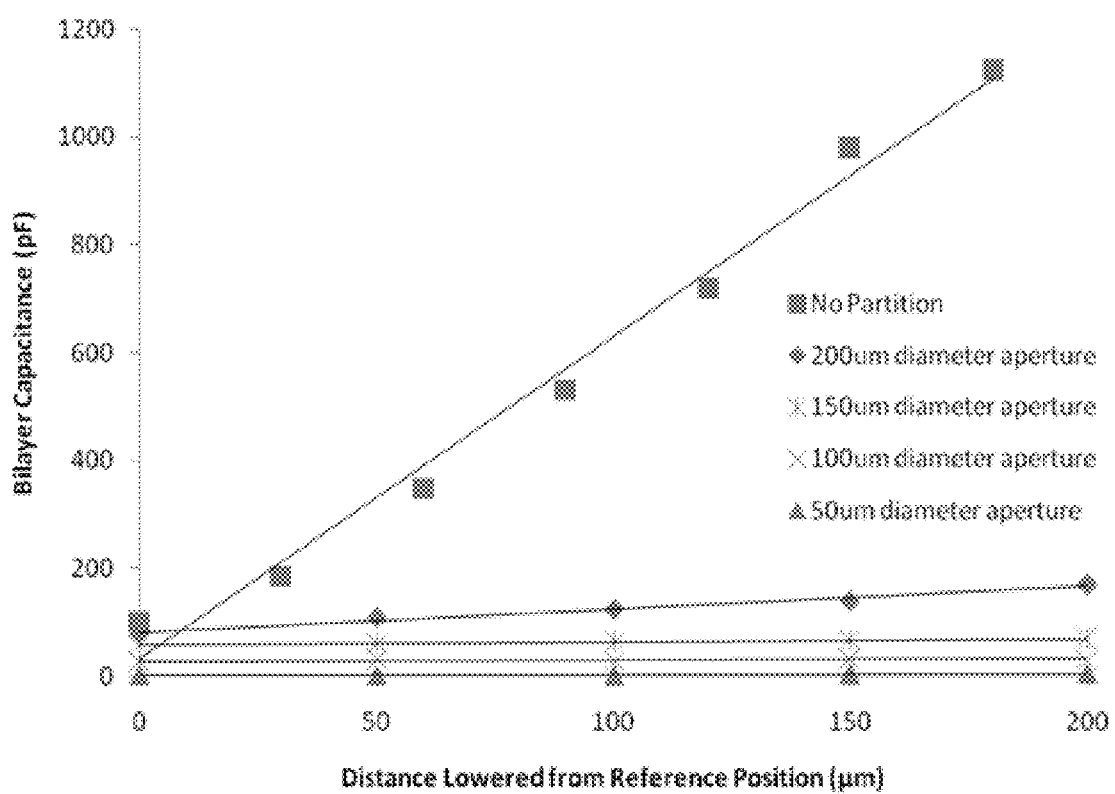
FIG. 2 shows the bilayer capacitance as a function of vertical pin position with masking apertures of diameter (50-200 µm) and with no aperture. The apertures allow control of bilayer area and strongly reduce its dependence on pin vertical position.

It was previously demonstrated that an apparatus for lipid bilayer formation and measurement using sessile droplets suspended from silver pins compatible with automated motion control and fluid handling technologies. (Poulos J L 2010) We and others ((Heron A J 2007; Poulos J L 2010))) have shown that the bilayer capacitance (proportional to area) is strongly dependent on the contact area of the aqueous phases, which can be affected by their positioning and size. Specifically, it was shown that the bilayer capacitance (proportional to area) varied approximately linearly with the upper droplet's vertical position (FIG. 2). As shown, the measured capacitance increases from 102 pF to 186 pF as the droplet is lowered 30 μm.

From this it was estimated that, to obtain 10% repeatability in bilayer capacitance and area, the relative position of the aqueous fluid interfaces must be precise within 3.6 μm. This relative position is determined by the position of the pin holding the sessile droplet, the volume of sessile droplet, and the position of the lower aqueous interface, which itself depends on the volume of the lower fluids and the dimensions of the channels and wells. Estimating the shape of the 2.5 μl sessile droplet on the pin as a spherical cap, 3.6 μm precision in height of this droplet corresponds to 15 nl required precision in droplet volume. Further, for development of parallel arrays, this vertical precision also requires a high degree of machining tolerance, uniformity, and alignment of the component parts.

With masking apertures in Delrin films between 50 and 200 μm in diameter, formation and measurement of stable bilayers were highly repeatable, with the bilayer area controlled by the pore size (FIG. 2). The dependence of bilayer capacitance on vertical and lateral relative positions of the aqueous interfaces was significantly diminished when using the aperture mask (FIGS. 2 and 3). A change in the capacitance of a masked bilayer of 10% only resulted after vertical displacements of >100 μm for the 50, 100, 150 μm apertures and <50 μm for the 200 μm masks. Similarly, the dependence of measured capacitance on lateral droplet alignment was markedly reduced with 150 μm aperture as compared to no aperture. With the aperture, consistent bilayer sizes resulted even with the pin positioned over 400 μm from the well center.

Easy control and repeatability of bilayer size allows the number of incorporated ion channels to be specified as can be the level of measurement noise associated with the bilayer capacitance (Wonderlin W F 1990). This was observed to decrease as aperture size and bilayer capacitance decreased and was accomplished solely through reduction in the aperture size, holding constant the apparatus and volumes and positions of the fluids.

In addition, of key technological importance is the ability to support solution exchange. Without the masking aperture, pumping of the lower solution significantly displaced the fluidic interfacial boundary, rupturing the bilayer even at low flow rates (<1 ml/hr). However, with the mask, it was obtainable to flow solution through the lower chamber, stop the flow, and resume measurement, simulating an experiment in which analyte concentration in the lower solution is changed. Measuring of bilayers was also possible during exchange at flow rates at rates of up to 20 ml/hr (FIG. 4). Data from two bilayers are shown, demonstrating that the measured bilayer capacitance remains within 10% of its original value.

Solution exchange enables increased experimental throughput by allowing for a variety of different experimental conditions to be tested in a short time, as well as measuring the activity of a large but fixed number of ion channels in the presence of varying concentrations of pharmaceutically active compounds for $IC_{50}/EC_{50}$ determination.

(c) Conclusion

This type of apparatus enables automated, repeatable high yield formation and measurement of artificial lipid bilayers and ion channels incorporated into them. This goal is achieved by constraining the bilayer area using a masking aperture, which were superior in performance compared to their absence. The devices using these apertures are easily arrayable to result in multi-well plates for parallel bilayer and ion channel measurements. This parallelization, in combination with improved compatibility of bilayer formation with automation and the ability to support solution exchange without disturbing the bilayer, can result in significantly increased throughput ion channel studies using artificial bilayers.

6. Example 2

Ion Channel Drug Potency Assay with an Artificial Bilayer Chip

The potency of pharmaceutical compounds acting on ion channels can be determined through measurements of ion channel conductance as a function of compound concentration. Described herein is artificial lipid bilayer apparatus for simple, fast, and high yield measurement of ion channel conductance with simultaneous solution perfusion. In this example the application of this chip to the measurement of the mammalian cold and menthol receptor TRPM8. Ensemble measurements of TRPM8 as a function of concentration of menthol and 2-aminoethoxydiphenyl borate (2-APB), enabled efficient determination of menthol's $EC_{50}$ (111.8 µM±2.4 µM) and 2-APB's $IC_{50}$ (4.9 µM±0.2 µM) in agreement with published values. This validation, coupled with the compatibility of this platform with automation and parallelization, indicates significant potential for large scale pharmaceutical ion channel screening.

(a) Introduction

Electrophysiological measurements of ion channels are important scientifically and pharmacologically. The potency of pharmaceutical compounds on ion channels can be shown through measured changes in ion channel conductance as a function of compound concentration and expressed in the form of $IC_{50}$ and $EC_{50}$ concentrations. These are commonly measured with cells using the patch clamp technique (B. Sakmann et al., *Ann. Rev. Physiol.*, 1984, 46, 455-472; J. A. Fernández, et al., *J. Gen. Physiol.*, 2011, 137, 173-195).

Artificial lipid bilayers are well established for reconstitution and study of ion channels at the single-channel level and have been used to contain pore proteins for sensing applications (E. Zakharian, et al., *J. Neurosci.*, 2010, 30, 12526-12534; J. J. Kasianowicz, et al. *Natl. Acad. Sci. U.S.A.*, 1996, 93, 13770-13773). Their particular advantages include simplified apparatus and the high degree of control over the membrane composition and surrounding solution. There have been a number of recent developments in artificial bilayer platforms with improved robustness and longevity, microfluidic integration, and parallelization, which indicate the potential of this technology to widen its range of applicability (M. Hirano, et al., *J. Surf. Sci. Nanotechnol.*, 2008, 6, 130-133; T.-J. Jeon, et al., *J. Am. Chem. Soc.*, 2006, 128, 42-43; H. Suzuki, et al., *Langmuir*, 2006, 22, 1937-1942; T. Ide, et al., *Anal. Chem.*, 2008, 80, 7792-7795; G. Baaken, et al., *Lab Chip*, 2008, 8, 938-944; G. Baaken, et al., *ACS Nano*, 2011, 5, 8080-8088). In particular, artificial bilayers formed through mechanical contact of lipid monolayers at aqueous/oil interfaces or droplets (L. Tsofina, et al., *Nature*, 1966, 212, 681-683; K. Funakoshi, et al., *Anal. Chem.*, 2006, 78, 8169-8174; M. A. Holden, et al., *J. Am. Chem. Soc.*, 2007, 129, 8650-8655; S. H. White, The physical nature of planar bilayer membranes in *Ion Channel Reconstitution*, Plenum Press, New York, 1986) have enabled implementation in microfluidic devices (M. Zagnoni, et al., *Biosens. Bioelectron.*, 2009, 24, 1235-1240; N. Malmstadt, et al., *Nano Lett.*, 2006, 6, 1961-1965), automation (J. L. Poulos, et al., *J. Phys.-Condens. Mat.*, 2010, 22, 454105; J. L. Poulos, et al., *Biotechnol. J.*, 2010, 5, 511-514; T. Thapliyal et al., *Biosens. Bioelectron.*, 2011, 26, 2651-2654), and arrays (S. Leptihn, et al., *J. Am. Chem. Soc.*, 2011, 133, 9370-9375; J. L. Poulos, et al., *Biosens. Bioelectron.*, 2009, 24, 1806-1810; et al., *Adv. Mater.*, 2007, 19, 4466-4470). These developments in artificial bilayer platforms have the potential to make practical their use in pharmaceutical ion channel screening, alongside automated and parallelized patch clamp platforms (J. Dunlop, et al., *Nat. Rev. Drug Discov.*, 2008, 7, 358-368). Syeda et al. screened a single viral potassium channel Kcv by serially contacting droplets containing Kcv to drug-containing droplets (R. Syeda, et al., *J. Am. Chem. Soc.*, 2008, 130, 15543-15548). Recently, Leptihn et al. showed measurements of mammalian and human ion channels in droplet bilayers obtained from cells and organelles (S. Leptihn, et al., *J. Am. Chem. Soc.*, 2011, 133, 9370-9375).

Conventional electrophysiological ion channel screening predominantly involves measurements of ensemble ion channel currents in the presence of pharmaceutical compounds at varying concentration (H. Chuang, et al., *Neuron*, 2004, 43, 859-869; H.-Z. Hu, et al., *J. Biol. Chem.*, 2004, 279, 35741-35748). Recently, we described the stabilization of interface bilayers using a mask that allows solution perfusion and compound exchange adjacent to the bilayer (S. A. Portonovo et al., *Biomed. Microdevices*, 2011, DOI: 10.1007/s10544-011-9596-5). Here we used a chip containing such a mask to rapidly and efficiently measure the cold and menthol sensing ion channel TRPM8 at the single-channel and ensemble level.

TRPM8, a member of the Transient Receptor Potential Melastatin (TRPM) family (N. Kedei, et al., *J. Biol. Chem.*, 2001, 276, 28613-28619; T. Rosenbaum, et al., *BMC Neurosci.* 2002, 3, 4-13), was the first temperature-activated channel found to sense cold (A. M. Peier, et al., *Cell*, 2002, 108, 705-715; D. D. McKemy, et al., *Nature*, 2002, 416, 52-58), and has become a primary target in studies of thermosensation and cold stimulating compounds (J. A. Fernández, et al., *J. Gen. Physiol.*, 2011, 137, 173-195; E. Zakharian, et al., *J. Neurosci.*, 2010, 30, 12526-12534; E. Zakharian, et al., *PLoS One*, 2009, 4, e5404; D. Andersson, et al., *J. Neurosci.*, 2004, 24, 5364-5369; S. Brauchi, et al., *P. Natl. Acad. Sci. U.S.A.*, 2004, 101, 15494-154999; H.-J. Behrendt, et al., *Br. J. Pharmacol.*, 2004, 141, 737-745). TRPM8 has been identified with multiple cancer types (L. Zhang et al., *Endocr. Relat. Cancer*, 2006, 13, 27-38; L. Tsavaler, et al., *Cancer Res.*, 2001, 61, 3760-3769), and a TRPM8 antagonist reduces symptoms of painful bladder syndrome in rats (E. S. R. Lashinger, et al., *Am. J. Physiol. Renal Physiol.*, 2008, 295, 803-810). With diverse roles in multiple tissues and relevance for cancer and pain therapy, TRPM8 is an important drug discovery target.

The measurements of TRPM8's single channel conductance, temperature response, and phospholipid sensitivity agreed well with previously published studies. Measurements of TRPM8 ensembles during perfusion of solutions of menthol and 2-aminoethoxydiphenyl borate at varying concentrations enabled us to efficiently determine the $EC_{50}$ and $IC_{50}$ values of these compounds with TRPM8, also in agreement with the literature. These results, combined with the simplicity and high yield of this platform and its compatibility with automation and parallelism, show great promise for lipid bilayers to play a role in ion channel drug discovery and safety screening.

(b) Materials and Methods

Unless otherwise noted, all reagents and chemicals were purchased from Sigma Aldrich.

The general apparatus for these experiments is described in Example 1. The apparatus was prepared for use by filling the outer wells and lower channel with 200 µL of an aqueous solution containing liposomes (described below) (FIG. 1B). The 200 µm aperture in the hydrophobic Delrin film is sufficiently small to prevent flow of aqueous solution through it. 80 µL of n-decane was then added to the center well, contacting the lower aqueous solution through the Delrin aperture (FIG. 1B). A Ag/AgCl pin electrode with 2 µL sessile droplet of aqueous liposome solution was introduced to the decane in the center well (FIG. 1B) (J. L. Poulos, et al., *J. Phys.-Condens. Mat.*, 2010, 22, 454105). Using a micromanipulator, the pin and droplet were lowered to the Delrin aperture to obtain lipid bilayer formation through the contact of the lipid monolayers formed on both aqueous/decane interfaces, as previously described (S. A. Portonovo and J. J. Schmidt, *Biomed. Microdevices*, 2011, DOI: 10.1007/s10544-011-9596-5). The lower aqueous solution could be exchanged by adding and withdrawing fluids through the outer wells (FIG. 1B).

(c) TRPM8 Reconstruction

A TRPM8 construct with 6× histidine tag at the amino terminus was transformed into *E. coli*, expressed, and purified. Following purification, TRPM8 was reconstituted into liposomes, adapted from Long et al. (S. B. Long, et al, *Nature*, 2007, 450, 376-382) 200 nm diameter unilamellar liposomes were prepared, composed of 1-palmitoyl-2-oleoyl-sn-glycero-3-phosphocholine (POPC) and 1-palmitoyl-2-oleoyl-sn-glycero-3-phosphoethanolamine (POPE) (Avanti Polar Lipids) at a ratio of 3:1 (w:w).[39,40] Purified TRPM8 was reconstituted into these liposomes at protein:lipid ratios (w:w) of 1:100, 1:1,000, and 1:10,000. The resulting proteoliposomes were aliquoted and stored at −80° C. Detailed procedures and protocols are contained in the Supplementary Information.

TRPM8 proteoliposomes were diluted to a final concentration of 1 mg/mL in reconstitution buffer (RB, 20 mM HEPES (pH 7.2), 150 mM KCl, 0.2 mM $MgCl_2$). 2 µL of this solution was used for the sessile droplet and 200 µL of this solution (or a similarly prepared liposome solution not containing TRPM8) was added to the lower aqueous channel.

(d) Electrophysiological Measurement

A Ag/AgCl counter electrode placed in the one of the outer wells and the Ag/AgCl pin electrode were connected to an Axopatch 200B amplifier (Axon Instruments), which was used to apply a transmembrane potential and measure the resultant ionic current (FIG. 1B). The signals were digitized with a Digidata 1332A (Axon Instruments) at 10 kHz, filtered in hardware with a 1 kHz Bessel filter, filtered post-acquisition with a 200 Hz Bessel filter and analyzed with Clampfit10 software (Axon Instruments). Bilayer capacitance was measured throughout to ensure that changes in measured current were due to changes in channel conductance and not changes in bilayer size or stability.

Temperature was measured using a 10 kΩ n-type thermistor (Newark) placed in the solution of one of the outer wells. The thermistor was connected in series with a 10 kΩ resistor (Newark) to form a voltage divider; resistor voltage was recorded using a BNC-2110 connector block and PCI-6036E DAQ Card (National Instruments) and used to determine resistance and temperature with LabVIEW 9.2.1 (National Instruments). Experiments were performed at room temperature, ~20° C., unless otherwise mentioned. An alcohol lamp was placed near the bilayer chamber to gently heat the experimental environment for temperature experiments.

Figures 6A, 6B, 6C:
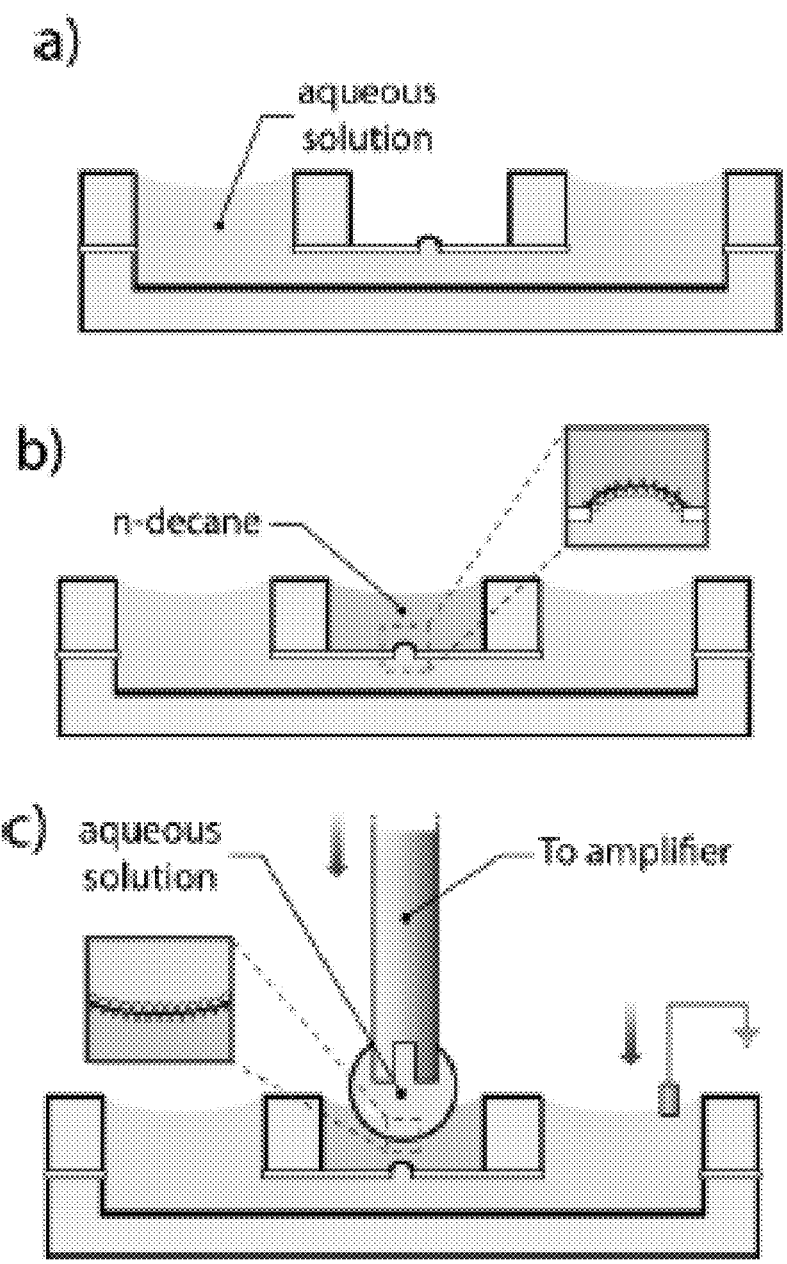
FIG. 6A-6D show a droplet bilayer apparatus use. (a) The lower channel was filled with an aqueous solution containing TRPM8 proteoliposomes (1 mg mL21 in 20 mM HEPES (pH 7.2), 150 mM KCl, 0.2 mM MgCl2). (b) The central well was then filled with n-decane, resulting in lipid monolayer formation at the aqueous-decane interface, restricted by the aperture in the Delrin film. (c) 2 mL of proteoliposome solution was then deposited on the bottom of a Ag/AgCl pin electrode. The electrode was lowered, via a micromanipulator, into the central well to allow a lipid monolayer to form at the droplet interface. After approximately five-minutes dwell time, the pin was lowered to contact the monolayers on the aqueous interfaces in order to form a bilayer. (d) Drug dosing was achieved through the addition and withdrawal of solution from the lower channel via the fluid inlet and fluid outlet lines. Electrical measurements of the bilayer were made by the pin electrode and Ag/AgCl counter electrode (inserted into the outlet well).
Figure 6D:
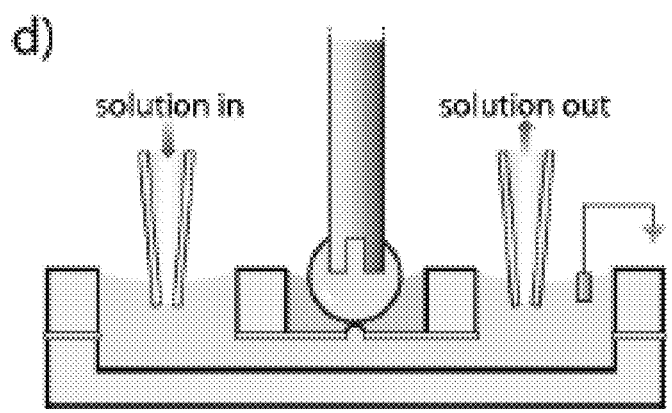

Short-chain phosphatidylinositol-4,5-bisphosphate (PI(4,5)$P_2$) (Avanti Polar Lipids), menthol and 2-APB were dissolved in RB to a final concentration of 100 µM, 2 mM, and 300 µM, respectively. During measurement, solutions were added to the fluid inlet well and withdrawn from the fluid outlet well (FIG. 6D).

(e) Results

Bilayers were formed with this chip at very high yield and with highly consistent diameters (163±14 µm (n=55), measured capacitively).[17] Following bilayer formation, a potential of 0 mV was applied followed by voltage steps from −100 mV to +100 mV, in 20 mV increments for 10 seconds each, and the resulting current measured. We measured no TRPM8 currents in the absence of the signaling phospholipid PI(4,5)$P_2$, in agreement with previous work (B. Liu and F. Qin, *J. Neurosci.*, 2005, 25, 1674-1681; T. Rohács, C. M. B. Lopes, I. Michailidis and D. E. Logothetis, *Nat. Neurosci.*, 2005, 8, 626-634). Hence, in all experiments PI(4,5)$P_2$ was present in the measurement buffer at 2.5 µM. With PI(4,5)$P_2$, constant TRPM8 currents were almost always observed immediately upon bilayer formation. Use of proteoliposomes with protein:lipid of 1:10,000 resulted in TRPM8 measurement at approximately the single-channel level, whereas ratios of 1:100 and 1:1,000 resulted in measurement of hundreds of channels.

Figure 10:
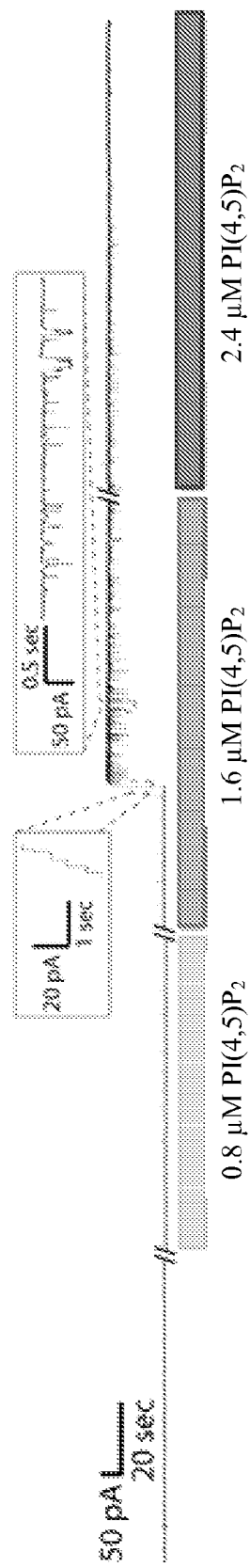
FIG. 10 shows the ensemble recordings of TRPM8 currents while varying PI(4,5)P$_2$ concentration in the presence of 250 µM menthol and a clamping potential of +100 mV. Data were filtered at 200 Hz. Measurements began in the absence of PI(4,5)P$_2$. After ten minutes at each concentration, the concentration of PI(4,5)P$_2$ was then increased by 0.8 µM with the addition of 2.4 µL PI(4,5)P$_2$ stock solution (100 µM) to the 200 µL lower aqueous solution. With no PI(4,5)P$_2$ in the measurement solution, there was no observed channel activity. As the concentration of PI(4,5)P$_2$ increased, frequency of channel opening increased. At 2.4 µM PI(4,5)P$_2$, the maximum current did not increase further. Throughout experiments, temperature was kept constant at 20° C.
Figures 11A, 11B:
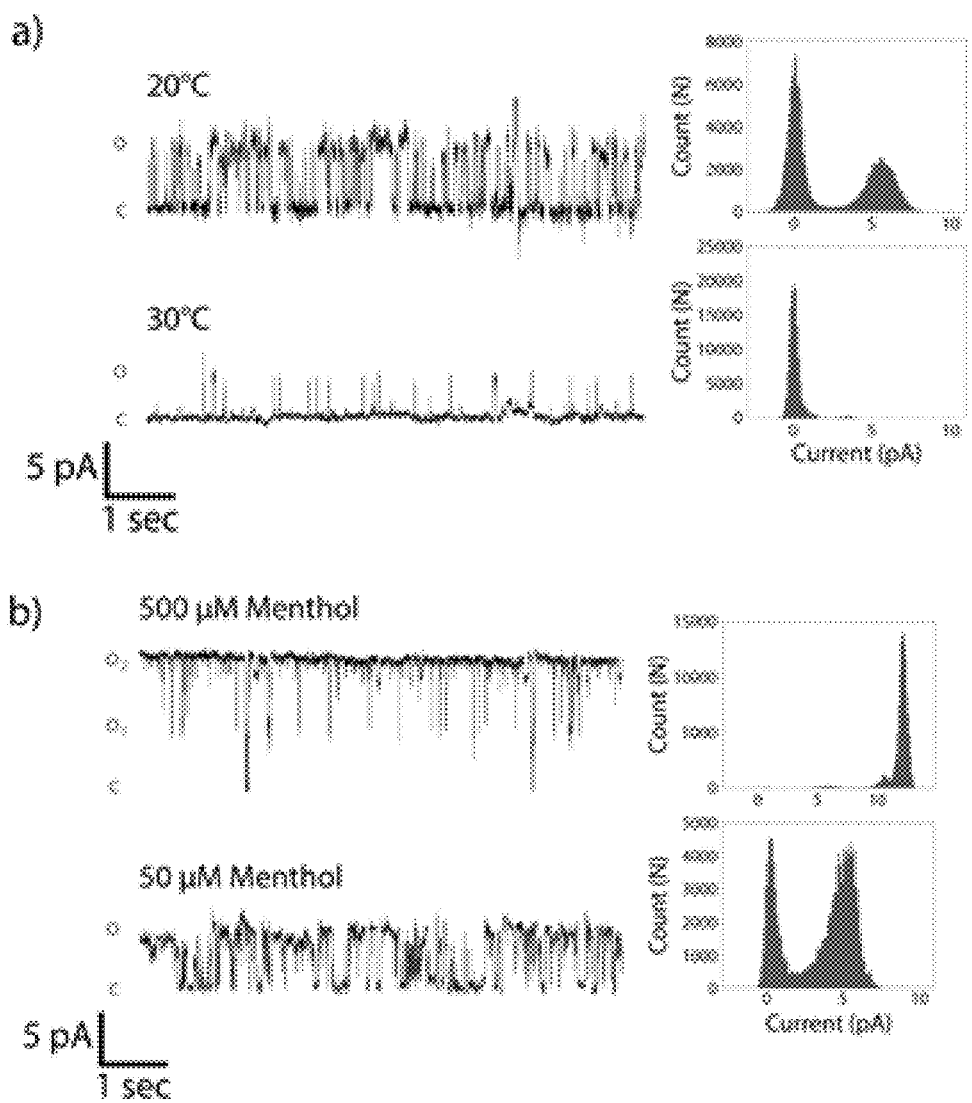
FIGS. 11A and 11B show the cold and menthol activation of TRPM8 respectively. Representative single-channel recordings (left panels) and corresponding all points' histograms (right panels) shown with applied potential of +100 mV. Data were filtered at 200 Hz. All single-channel measurements were done using proteoliposomes of a protein:lipid ratio of 1:10,000 (w:w).

Measurements of single channel conductance (64±6 pS (n=21) and open probability as a function of temperature (30° C.: $P_{open}$=0.035±0.012 (n=7); 20° C.: $P_{open}$=0.410±0.035 (n=7)) (FIG. 11A), matched previously published values (J. A. Fernández, et al., *J. Gen. Physiol.*, 2011, 137, 173-195; E. Zakharian, et al., *J. Neurosci.*, 2010, 30, 12526-12534). Similar to the effect of decreasing temperature, at 20° C. menthol also activated TRPM8 in a concentration dependent manner increasing $P_{open}$ from 0.410±0.035 (n=7) at 0 µM (FIG. 10) to 0.639±0.029 (n=9) at 50 µM and 0.967±0.013 (n=9) at 500 µM (FIG. 11B). Ensembles of TRPM8 were measured using a 1:1000 protein:lipid ratio. The magnitude of measured currents varied widely between experiments. The average observed current over 20 experiments was 693.5±502.7 pA, corresponding to 108±79 channels based on the observed single channel conductance determined above. As described below, this variability did not affect drug potency measurements because, once reconstituted, the magnitude of the current and number of channels remained constant, enabling the relative change in channel conductance between experiments to be compared.

Figure 12:
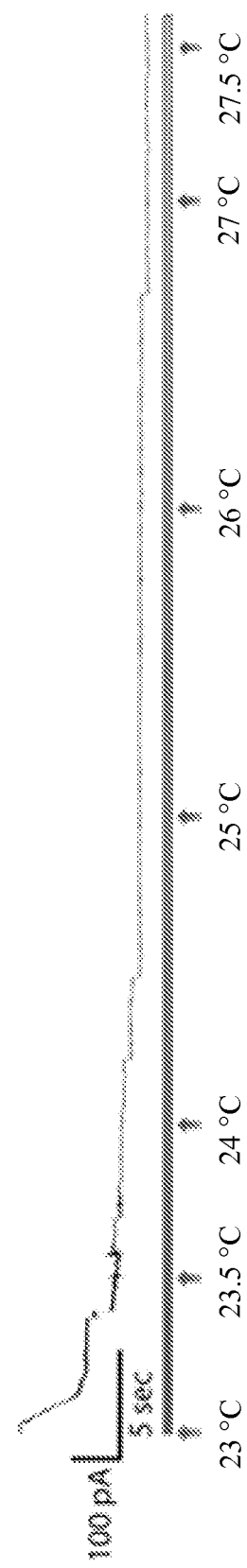
FIG. 12 shows the ensemble recordings of TRPM8 currents while varying temperature in the presence of 250 µM menthol and a clamping potential of +100 mV. Data were filtered at 200 Hz. Measurements made in the presence of 2.5 µM PI(4,5)P$_2$ and at a starting temperature of 20° C. After recording channel activity at 20° C. for five minutes, alcohol lamp was then ignited and chamber temperature was slowly increased to 35° C. In representative trace, maximal current (275 pA) was achieved at 20° C. and, upon warming, remained constant until 23° C. For temperatures greater than 23° C., the measured current progressively decreased and was finally extinguished at 28° C.

Similar to the single channel measurements, the channel ensembles were also responsive to temperature changes (FIG. 12), corresponding to previous studies which have shown that TRPM8 responds to temperature without the aid of secondary membrane components (D. M. Bautista, et al., *Nature*, 2007, 448, 204-208; R. W. Colburn, et al., *Neuron*, 2007, 54, 379-386). As a control, bilayers formed from liposomes without reconstituted TRPM8 were measured in identical conditions and the current did not exceed 10 pA while capacitance remained constant through temperatures greater than 38° C.

(f) Measurement of Menthol and 2-APB Potency

Figure 7A:
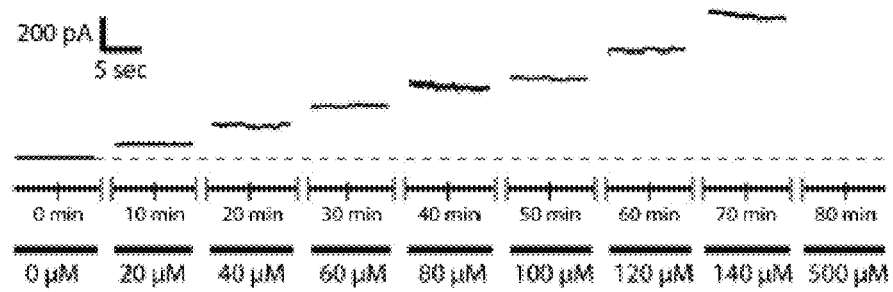
FIGS. 7A and 7B show a dose-dependent activation of TRPM8 by menthol and inhibition of menthol-evoked TRPM8 currents by 2-APB. Experiments were conducted using proteoliposomes at a protein:lipid ratio of 1:1000 diluted to 1 mg/mL in reconstitution buffer with 2.5 mM PI(4,5)P2 added. (a) Excerpts of one experiment in which the channel currents were continuously measured as menthol concentration was increased: 0 mM, 20 mM, 40 mM, 60 mM, 80 mM, 100 mM, 120 mM, 140 mM and 500 mM. Step-wise, dose-dependent increases in current were observed. (b) Excerpts of one experiment in which the channel currents (in the presence of 500 mM menthol) were continuously measured as 2-APB concentration was increased: 0 mM, 1 mM, 3.3 mM, 6.6 mM, 9.9 mM, and 13.2 mM. Dose-dependent decreases in current were observed following 2-APB addition.
Figure 7B:
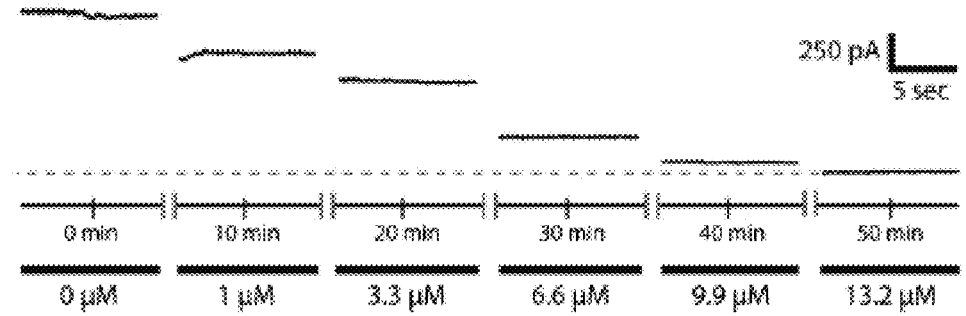

TRPM8 channels, reconstituted at a 1:1000 protein:lipid ratio, were measured with a +100 mV applied potential to measure menthol and 2-APB potency. The concentration of menthol, a TRPM8 activator, in the lower aqueous solution was increased from 20-140 µM in 20 µM increments and a final measurement at 500 µM. The resultant current at each concentration was measured over 10 minutes before the concentration was increased (FIG. 7). Likewise, TRPM8 currents were similarly measured with 2-APB, a TRPM8 inhibitor, at concentrations 1 µM, 3.3 µM, 6.6 µM, 9.9 µM, and 13.2 µM in solutions containing 500 µM menthol to activate TRPM8 (FIG. 7a). These experiments were repeated three times for each compound. In one experiment with 2-APB, we also measured concentrations of 5 µM, 9 µM and 11 µM.

Figure 8A:
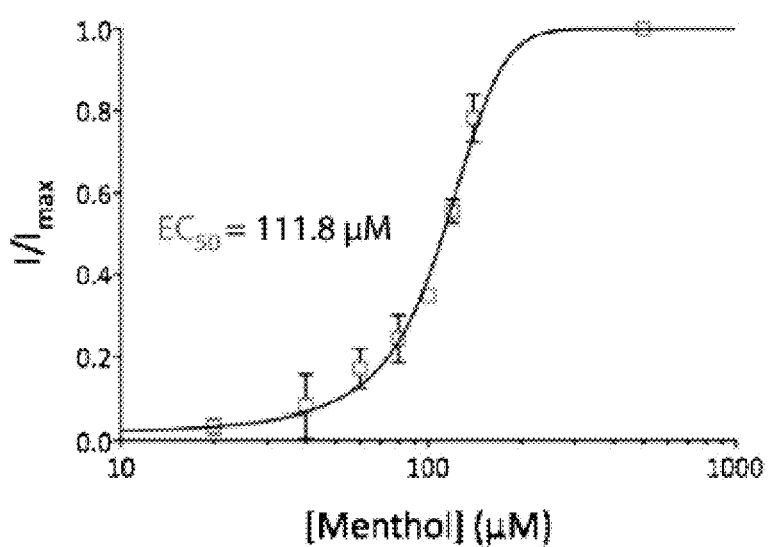
FIGS. 8A and 8B show $IC_{50}$ and $EC_{50}$ results for TRPM8 following menthol and 2-APB addition. Currents recorded (e.g.
Figure 8B:
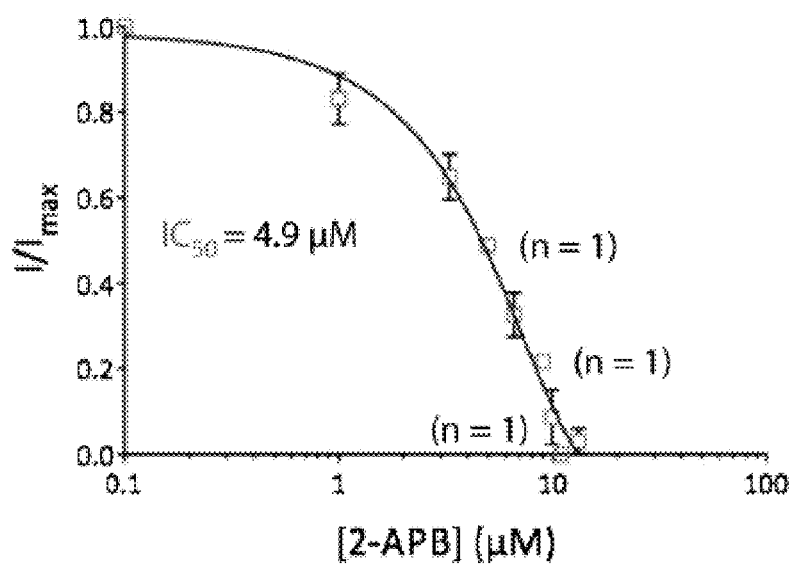

The average current at each concentration was determined and normalized by the maximum value measured. The normalized average currents were plotted as a function of menthol and 2-APB concentration (FIG. 8). These normalized currents were fitted to the following equation using GraphPad Prism software (GraphPad Ltd.):

$$\frac{I}{I_{max}} = \frac{1}{(1 + 10^{((\log A - X) \times Hill\ Slope)})}$$

where A is the $EC_{50}$ or $IC_{50}$ value and X is the concentration of menthol or 2-APB, respectively. From this fit, an $EC_{50}$ value for menthol was determined to be 111.8±2.4 µM, comparing well to literature values of 80 µM to 101 µM found using patch clamp (D. Andersson, H. W. N. Chase and S. Bevan, *J. Neurosci.*, 2004, 24, 5364-5369; L. Zhang and G. J. Barritt, *Endocr. Relat. Cancer*, 2006, 13, 27-38; I. Dragoni, E.

Guida and P. McIntyre, *J. Biol. Chem.*, 2006, 281, 37353-37360). The fit of the 2-APB experiments gave an $IC_{50}$ value of 4.9±0.2 µM, also comparing well to literature values of 7.7 µM to 12 µM (H.-Z. Hu, et al., *J. Biol. Chem.*, 2004, 279, 35741-35748; R. Eccles, *J. Pharm. Pharmacol.*, 1994, 46, 618-630; A. Zholos, *Brit. J. Pharmacol.*, 2010, 159, 1559-1571).

(g) Discussion

Droplet bilayers have been the subject of much recent activity in part because bilayer formation results from a mechanical step, which is simple and highly amenable to automation and parallelization. Coupled with solution perfusion (S. A. Portonovo, Biomed. Microdevices, 2011, DOI: 10.1007/s10544-011-9596-5), they have considerable potential for pharmaceutical screening of ion channels, as well as greatly reducing the time and expertise required for ion channel measurement in bilayers. Toward this goal, we aimed to validate this platform through ensemble measurements of TRPM8 in the presence of agonist and antagonist compounds, menthol and 2-APB, respectively, and the determination of their $EC_{50}$ and $IC_{50}$ values enabled by solution perfusion.

Formation of interface bilayers was simple and fast, requiring only solution loading and mechanical translation of the center electrode, with less than 10 minutes elapsing from an empty chamber to bilayer measurement. The chamber design enabled electrical and fluidic access to both sides of the bilayer from the chamber top, allowing quick set up and convenient exchange of chambers between experiments. The experimental yield was excellent, with greater than 90% bilayer yield and successful TRPM8 measurements with most bilayers occurring immediately upon bilayer formation.

Control of membrane composition was important, as the presence of $PI(4,5)P_2$ was required for TRPM8 activity. Membrane composition is critical to the function of many ion channels, including those in the TRP family. The membrane composition in our system was specifiable through the prepared liposomes and amount of $PI(4,5)P_2$ added, and could be easily changed for studies with other ion channels or different membrane compositions. In situations in which a purely native membrane is desired or purified channels are unavailable, Leptihn et al. recently showed ion channel measurement from native cells in a similar droplet bilayer platform (*J. Am. Chem. Soc.*, 2011, 133, 9370-9375).

By varying the protein to lipid ratio or by diluting the proteoliposomes with protein-free liposomes of identical lipid composition, we could control the number of incorporated channels from one to thousands. The measured single channel conductance and dependence of open probability on temperature and menthol agreed well with previously published studies.

The variability in number of incorporated channels did not adversely affect drug-response measurements as a result of the ability of our platform to support solution perfusion during bilayer measurement, since the relative change in conductance was measured as a function of varying compound concentration over the same experiment. The determination of $IC_{50}$ and $EC_{50}$ values for drug potency in this way is standard in patch clamp measurements. The measured $IC_{50}$ and $EC_{50}$ values of 2-APB and menthol are in agreement with the literature (H.-Z. Hu, et al., *J. Biol. Chem.*, 2004, 279, 35741-35748; D. Andersson, et al., *J. Neurosci.*, 2004, 24, 5364-5369; L. Zhang et al., *Endocr. Relat. Cancer*, 2006, 13, 27-38; I. Dragoni, et al., *J. Biol. Chem.*, 2006, 281, 37353-37360; R. Eccles, *J. Pharm. Pharmacol.*, 1994, 46, 618-630; A. Zholos, *Brit. J. Pharmacol.*, 2010, 159, 1559-1571).

(h) Conclusion

TRPM8 measurements at the single channel and ensemble level matched well with previously published results as did the determined $IC_{50}$ and $EC_{50}$ values of 2-APB and menthol. The bilayer chip allowed electrical and fluidic access from the chamber top, allowing quick set up and convenient exchange of chambers between experiments. This chip design is also easily arrayed and compatible with parallel-automated fluid handling and motion control hardware.

With solution perfusion, concentration-dependent modulation of channel conductance by pharmaceutical candidates may be measured rapidly and repeatedly in parallel, giving it considerable potential for high throughput electrophysiological screening.

7. Example 3 hERG Response Measured in Droplet Bilayers

Described herein are measurements of the human cardiac potassium ion channel $K_v11.1$ (hERG) in droplet bilayers incorporated directly from commercial membrane preparations of HEK293 cells. Ensemble currents showed inhibition dependent on astemizole and E-4031 concentration with $IC_{50}$ values in good agreement with prior art measurements. The availability of engineered HEK cells expressing a variety of ion channels, combined with the simplicity of the inhibition measurement, suggest that droplet bilayers may have considerable technological potential for determination of ion channel drug potency.

(a) Introduction

Ion channel conductance measurements are used to determine drug potency and also detect off-target drug interactions, most commonly for the cardiac potassium ion channel $K_v11.1$ (hERG). (Hancox, McPate et al. 2008). In these measurements, inhibition (or enhancement) of the conductance is measured as a function of drug concentration, from which the $IC_{50}$ (or $EC_{50}$) is determined, defined as the concentration for which the measured channel conductance is 50% of the maximum. Ion channel drug inhibition can also be determined optically through radioligand binding, (Chiu, Marcoe et al. 2004; Diaz, Daniell et al. 2004) measurements of ion flux, (Cheng, Alderman et al. 2002; Titus, Beacham et al. 2009; Schmalhofer, Swensen et al. 2010) or membrane potential. (Falconer, Smith et al. 2002). Although these methods are not as information-rich as electrophysiological measurements, they allow $IC_{50}$ determination for lower cost and higher throughput.

Electrophysiological measurements of ion channel conductance are predominantly made from ion channel ensembles in whole cells using patch clamp. Ion channel ensembles have also been measured in lipid bilayers, (Schindler and Rosenbusch 1978; Schindler and Quast 1980; Tao and MacKinnon 2008; Leptihn, Thompson et al. 2011; Brohawn, del Marmol et al. 2012; El-Arabi, Salazar et al. 2012) which offer simplified apparatus, reduced training, and the ability to easily control membrane and solution composition. Droplet interface bilayers (DIBs) (Funakoshi, Suzuki et al. 2006; Holden, Needham et al. 2007) have shown promise technologically, supporting automation and parallelism, (Ide, Kobayashi et al. 2008; Poulos, Portonovo et al. 2010) which may indicate significant potential for this platform for ion channel screening. Reconstitution of ion channels in lipid bilayers directly from cellular membrane preparations simplifies protein expression, eliminates most purification steps, and is well established for measurement at the single channel (Schein, Colombini et al. 1976; Golowasch, Kirkwood et al.

1986; Yuan, O'Connell et al. 2004) and ensemble levels. (Schindler and Quast 1980) Schindler and Quast prepared vesicles from *Torpedo marmorata* containing acetylcholine receptor (AChR) and used them to form lipid monolayers at the air-water interface in a variant of Montal-Mueller bilayer formation (Schindler and Quast 1980). They observed ion channel currents, at single channel to ensemble levels depending on the amount of dilution of the prepared vesicles, which were activatable and inhibitable by AChR-active compounds. Recently Leptihn and co-workers showed a similar process using droplet bilayers, in which ion channel-containing membrane preparations were used to form lipid monolayers at oil-water interfaces before bilayer formation, measuring a variety of ion channels, including hERG (Leptihn, Thompson et al. 2011).

The suitability of DIBs for ion channel drug potency measurements was investigated. Concentration dependent drug activation and inhibition was previously measured of the rat cold and menthol sensitive ion channel TRPM8, which was expressed in *E. coli*, purified, and reconstituted into proteoliposomes for measurement in DIBs (El-Arabi, Salazar et al. 2012). However, this result is not readily generalizable because very few physiologically relevant ion channels have been successfully expressed in bacterial expression systems. The apparatus described in Example 1 was used during ion channel measurement and used it to measure the dose-dependent attenuation of hERG conductance from increasing concentrations of astemizole and E-4031. Analysis of the conductance as a function of drug concentration enabled determination of $IC_{50}$ values for these drugs comparable to published values (Zhou, Gong et al. 1998; Chachin, Katayama et al. 1999). These results, combined with the large variety of ion channels expressed in engineered HEK cells and the technological potential of droplet bilayers, indicate considerable promise for this platform in ion channel drug potency measurements.

(b) Materials and Methods

Membrane preparations of hERG-expressing HEK293 cells (Millipore) were used without further purification and analyzed with Western blots. Schindler and Quast showed that activity of AChR membrane preparations varied widely between different preparations. (Schindler and Quast 1980) Therefore, we did not quantify the amount of hERG present in the source material; rather, like Schindler and Quast (Schindler and Quast 1980) and Leptihn and coworkers, (Leptihn, Thompson et al. 2011), we empirically determined the appropriate dilution for ensemble and single channel measurement. Membrane preparations were diluted from 1:100,000 to 1:1,000,000 in measurement buffer (MB: 350 mM KCl, 10 mM HEPES, pH 7.5). Diphytanoyl-phosphatidylcholine (DPhPC, Avanti Polar Lipids) was dissolved at 1% (wt/vol) in hexadecane (Sigma). Bilayer measurement chambers and droplet bilayer formation were similar to previous work. (Zagnoni, Sandison et al. 2009; El-Arabi, Salazar et al. 2012; Portonovo and Schmidt 2012) Each chamber consisted of a lower compartment and an upper compartment, connected by a 200 μm circular aperture in a 75 μm thick Delrin sheet. 200 μL of the diluted hERG preparation was added to the lower compartment, followed by the addition of 50 μL of DPhPC/hexadecane to the upper compartment (FIG. 1B). A 2 μL sessile droplet of hERG solution was deposited on an Ag/AgCl pin electrode made from 16 gauge silver wire (C. C. Silver and Gold). The droplet was lowered into the DPhPC/hexadecane solution for 15 minutes to allow lipid monolayer formation (Poulos, Portonovo et al. 2010) at the aqueous/organic interface (FIG. 1*b*). The droplet was then lowered into contact with the monolayer formed at the lower aqueous/organic interface, bounded by the Delrin masking aperture. An Ag/AgCl counter-electrode made from 22 gauge silver wire (Ted Pella) was inserted into a side well accessing the lower aqueous solution, which served as the ground electrode. Both electrodes were chloridized for at least 20 min in Clorox bleach. Transmembrane voltages and electronic measurement of ion channel currents were measured using an Axopatch 200B amplifier (Molecular Devices) and digitized with a Digidata 1332A (Molecular Devices) at a sampling rate of 20 kHz and unfiltered. Over the course of the experiment, any non-zero offset currents observed with 0 V applied potential were eliminated using hardware adjustment.

(c) Results and Discussion

Figure 13:
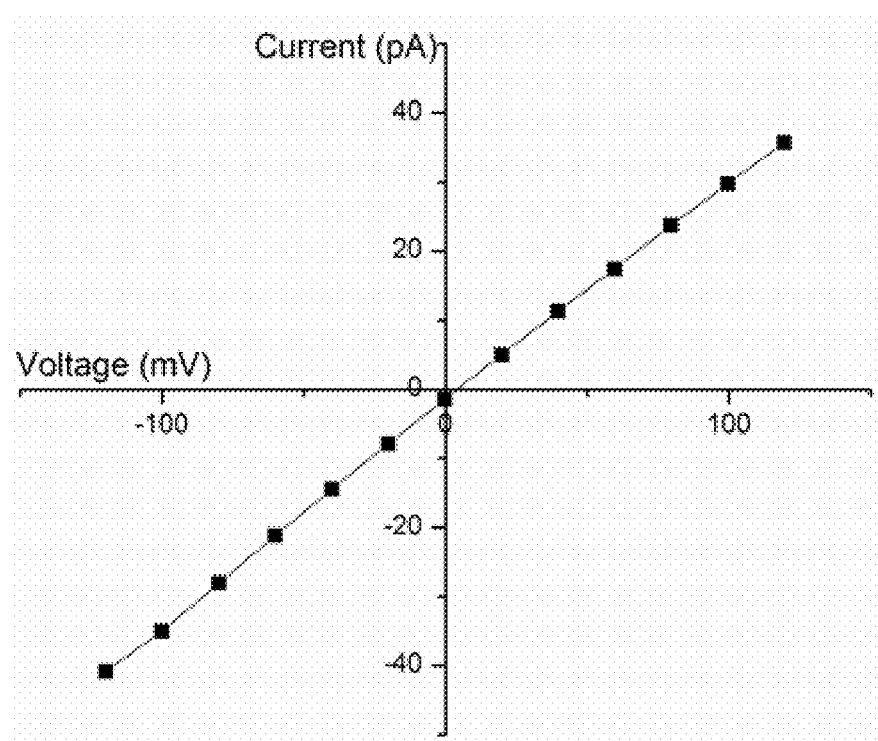
FIG. 13 shows a plot of current versus applied voltage obtained on a lipid bilayer produced with hERG membrane preparations.

Bilayer formation was observed capacitively after lowering the sessile droplet into contact with the lower aqueous interface. (Portonovo and Schmidt 2012) Since the same buffer was used on both sides of the bilayer, for ion channel measurement we applied similar transmembrane potentials as Kiehn and coworkers, who also measured hERG with the same solutions present on both sides of excised *Xenopus* oocyte membrane patches. (Kiehn, Lacerda et al. 1996) Specifically, they held the transmembrane potential at 0 V and stepped to voltages between −120 mV and +60 mV; the transmembrane potential was here held at 0 V for 2 seconds and stepped to voltages ranging from −120 mV to +120 mV for 10 seconds. At 1:100,000 dilution of the membrane preparations, currents was observed from tens to hundreds of pA. However, the ensemble kinetic activity and rectified conductance reported by Kiehn was not observed, (Kiehn, Lacerda et al. 1996) although the buffer conditions and applied voltages were similar. Instead, an ionic conductance was observed that was constant with respect to time and applied potential (FIG. 13). If the ion channels were reconstituted into the bilayer with symmetric orientation, it is expected that the magnitude of the measured current would be independent of the sign of the applied potential since the solutions on each side of the bilayer were the same. However, voltage activation and kinetics characteristic to hERG should still be seen. Therefore, in the absence of such observations, it is questionable whether these currents are attributable to the presence of hERG.

To explore this, astemizole and E-4031 was added to the lower aqueous solution during the experiment. Following bilayer formation and measurement of steady currents, solutions of MB containing either astemizole or E-4031 were added to the lower compartment of the measurement chambers in step-wise increasing concentrations. Astemizole is an anti-histamine drug no longer commercially available in many countries due to its role in producing cardiac arrhythmic side effects including Long QT syndrome. It is a known antagonist to voltage-gated potassium ion channels, including hERG. (Wulff, Castle et al. 2009)

Figure 9A:
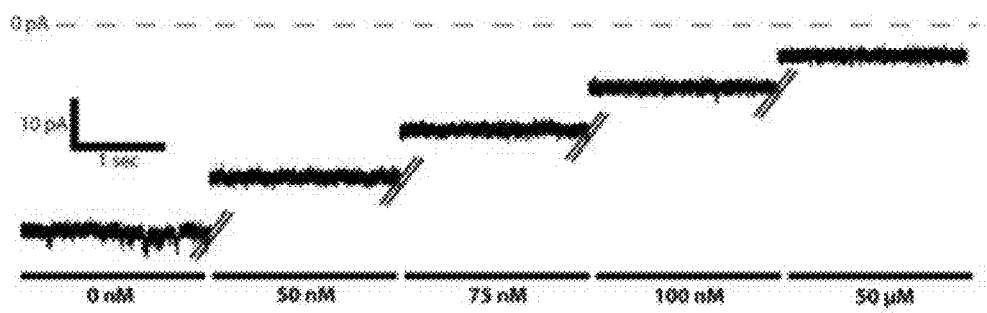
FIG. 9A-9D show: (a) Dose-dependence effect of astemizole on hERG currents. (Left) hERG currents measured following sequential application of solutions with increasing astemizole concentration shows dose-dependent inhibition, with a small amount of measured unblockable current remaining at high (50 µM) astemizole concentration (−100 mV applied). (Right) This unblockable current was subtracted from each measured current and the difference was normalized to the current measured before application of astemizole to result in the ratio $I/I_{max}$. This ratio was plotted versus astemizole concentration and fit to the Hill equation (see Example 3) to find the concentration at 50% conductance, $IC_{50}$. (b) (Left) hERG currents measured in increasing E-4031 concentration, with a small unblockable current at high (10 µM) E-4031 concentration (−100 mV applied). (Right) As with astemizole, the normalized blockable current ratio, $I/I_{max}$, was plotted versus E-4031 concentration and fit to the Hill equation to the $IC_{50}$ for E-4031. (c) Single channel hERG recording at −100 mV applied.
Figures 9B, 9C:
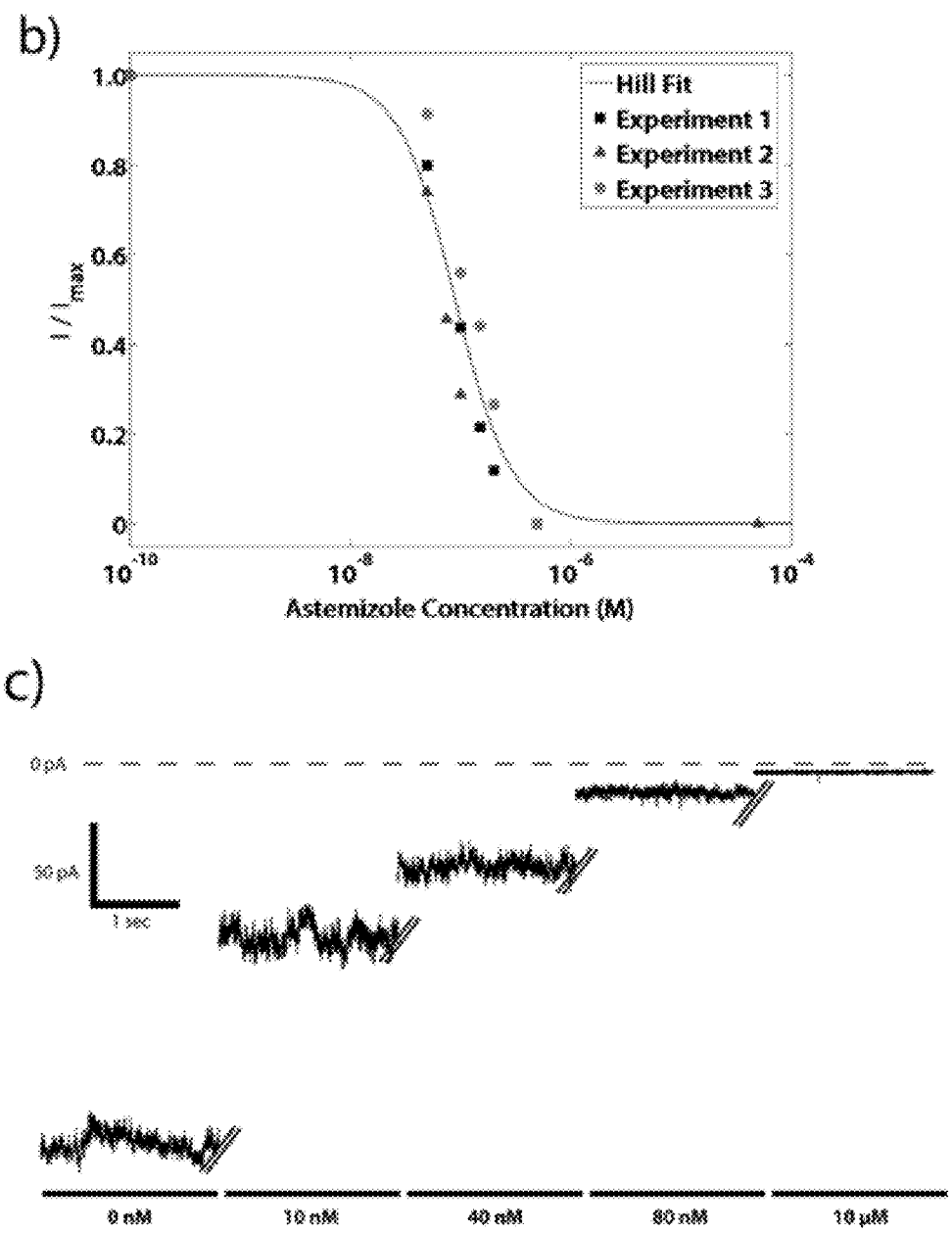
Figure 9D:
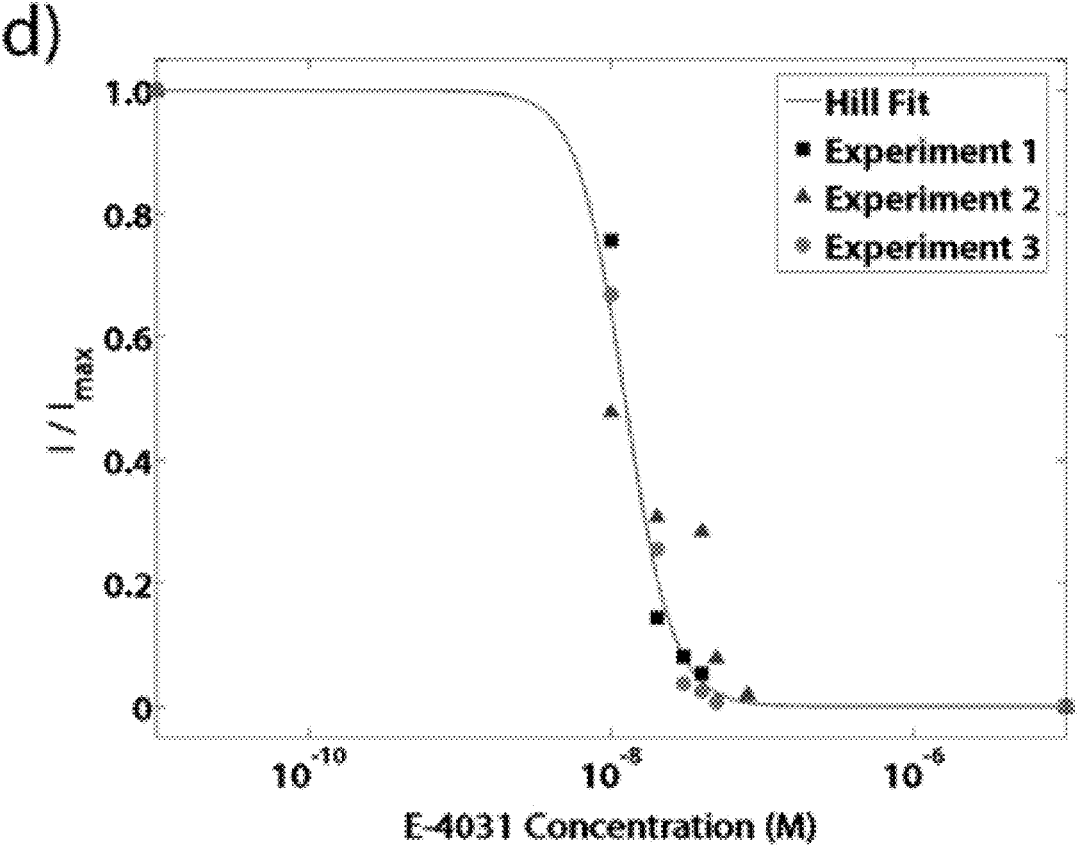

Astemizole (Sigma) was first dissolved in DMSO to yield a 10 mM stock solution, which was diluted to 5.0 μM in MB. 2 μL of this diluted astemizole solution was pipetted into one of the side wells of the bilayer chamber, followed by gentle agitation, resulting in a 50 nM solution of astemizole in the 200 μL lower chamber. Sequential additions of 1 μL of the diluted astemizole solution into the lower chamber increased the astemizole concentration to 75 nM, 100 nM, 150 nM, 200 nM, and 500 nM. Finally, 1 μL of the undiluted stock solution was added to achieve a 50 μM final concentration. After each dose of astemizole was added, ion currents were observed to decrease and eventually stabilize (FIG. 9). Additional solutions were added 5-10 minutes later. To confirm that the measured change in current did not result from changes in bilayer area or number of channels, the bilayer capacitance was measured throughout the experiment. In some experiments, small residual currents remained following administration of the final 50 μM solution concentration. The total fraction of DMSO in the measurement solution did not exceed 0.5%. In control experiments, identical amounts of astemizole and DMSO were added to DPhPC droplet bilayers made without hERG membrane preparations, with no change in membrane conductance observed.

Experiments using the hERG-specific blocker E-4031 (Sigma) were conducted similarly to those conducted with astemizole. E-4031 doses were sequentially added to the lower aqueous compartments of active bilayer chambers to produce resultant concentrations of 10 nM, 20 nM, 30 nM, 40 nM, 50 nM, 80 nM, and 10 μM. Currents were observed to decrease with each added dose of drug (FIG. 9c). As with astemizole, a small residual current was measured for the 10 μM concentration of E-4031. Control experiments applying E-4031 to DPhPC lipid bilayers without hERG did not produce ion currents. Each set of experiments was repeated at least three times for astemizole and E-4031.

To analyze the measured currents from each experiment, any unblockable current measured at the maximum concentration was subtracted from the current recorded for each concentration to obtain the magnitude of drug-responsive current. The ratio of this drug-responsive current to the maximum blockable current (obtained before administration of any drug) was plotted as a function of concentration to obtain dose-response plots for astemizole and E-4031 (FIGS. 9b and 9c). Curves were fit to these plots following the Hill equation:

$$\frac{I}{I_{max}} = \frac{1}{1 + 10^{(log_{10}[IC_{50}] - log_{10}[Drug]) * Hill\ Coefficient}}$$

using GraphPad Prism (GraphPad Ltd.) to obtain $IC_{50}$ values of 91 nM for astemizole and 12.4 nM for E-4031 and Hill coefficients of −1.98 and −2.35 for astemizole and E-4031, respectively. These values are similar to those reported in literature from whole-cell patch clamp experiments, which have been reported in ranges from 1-70 nM for astemizole and 8-48 nM for E-4031. (Zhou, Gong et al. 1998; Chachin, Katayama et al. 1999; Diaz, Daniell et al. 2004).

The reduction in current following the addition of astemizole and E-4031 with matching $IC_{50}$ values suggests that hERG channels are measured. Using a 1:1,000,000 dilution of the membrane preparations, we measured current spikes of magnitude 13.4±2.5 pS (Supplementary Material), comparable to previously reported hERG single channel currents at high ionic strength. (Zou, Curran et al. 1997) The absence of observed voltage and temporal conductance kinetics and voltage rectification echo the observations made by Schindler and Quast for membrane preparations of AChR reconstituted in lipid bilayers made from monolayers formed at air-water interfaces, which also did not display characteristic voltage dependent conductance or kinetics. (Schindler and Quast 1980) These similarities indicates that the hERG and AChR channels are affected similarly by their exposure to hexadecane and air, respectively, potentially limiting the scope of studies using droplet bilayers for measurement of ion channel ensembles. The measurements of constant hERG conductance also resemble those of Chen and coworkers, who generated a F656A/G657F hERG mutant which was constitutively open. (Chen, Seebohm et al. 2002)

It is shown that measurements of ionic currents in droplet lipid bilayers can be made from commercial membrane preparations of hERG-expressing HEK293 cells. Although these currents did not display the voltage activation and kinetics characteristic of published studies of hERG using patch clamp, the currents were inhibited by astemizole and the hERG-specific blocker E-4031, with $IC_{50}$ values measured in our system consistent with reported values. Such results can be closer to those provided by technologies indirectly measuring ion channel drug potency such as membrane potential and flux assays than they are to traditional patch clamp-based measurement.

8. References

Andersson, D., Chase, H. W. N. and Bevan, S. TRPM8 Activation by Menthol, Icilin, and Cold Is Differentially Modulated by Intracellular pH. *J. Neurosci.*, 2004, 24, 5364-5369.

Baaken, G., Ankri, N., Schuler, A. K., Rühe, J. and Behrends, J. C. Nanopore-Based Single-Molecule Mass Spectrometry on a Lipid Membrane Microarray. *ACS Nano*, 2011, 5, 8080-8088.

Baaken, G., Sondermann, M., Schlemmer, C., Rühe, J. and Behrends, J. C. Planar microelectrode-cavity array for high-resolution and parallel electrical recording of membrane ionic currents. *Lab Chip*, 2008, 8, 938-944.

Bautista, D. M., Siemens, J., Glazer, J. M., Tsuruda, P. R., Basbaum, A. I., Stucky, C. L., Jordt, S. E. and Julius, D. The menthol receptor TRPM8 is the principal detector of environmental cold. *Nature*, 2007, 448, 204-208.

Bayley H., Cronin, B., Heron A., Holden M. A., Hwang W., Syeda R., Thompson J., and Wallace M. Droplet interface bilayers. *Mol. Biosyst*, 2008, 4, 1191-1208.

Behrendt, H. J., Germann, T., Gillen, C., Hatt, H. and Jostock, R. Characterization of the mouse cold-menthol receptor TRPM8 and vanilloid receptor type-1 VR1 using a fluorometric imaging plate reader (FLIPR) assay. *Br. J. Pharmacol.*, 2004, 141, 737-745.

Blake, S., Mayer, T., Mayer, M. & Yang, J. Monitoring chemical reactions by using ion-channel-forming peptides. *Chembiochem* 7, 433-435 (2006).

Blaustein, R. O., Koehler, T. M., Collier, R. J. & Finkelstein, A. Anthrax Toxin—Channel-Forming Activity of Protective Antigen in Planar Phospholipid-Bilayers. *Proceedings of the National Academy of Sciences of the United States of America* 86, 2209-2213 (1989).

Braha, O., Walker, B., Cheley, S., Kasianowicz, J. J., Song, L., Gouaux, J. E. and Bayley H. Designed protein pores as components for biosensors. *Chemistry and Biology* 4, 497-505 (1997).

Braha, O., Gu, L. Q., Zhou, L., Xiaofeng, L., Cheley, S, and Bayley, H. Simultaneous stochastic sensing of divalent metal ions. *Nature Biotechnology* 18, 1005-1007 (2000).

Brauchi, S., Orio, P. and Latorre, R. Clues to understanding cold sensation: Thermodynamics and electrophysiological analysis of the cold receptor TRPM8. *Proc. Natl. Acad. Sci. U.S.A.*, 2004, 101, 15494-154999.

Brohawn, S. G., del Mármol J. and MacKinnon R. Crystal structure of the human K2P TRAAK, a lipid- and mechano-sensitive K+ ion channel. *Science;* 335(6067): 436-41 (2012)

Capone, R., Blake, S., Restrepo, M. R., Yang, J. & Mayer, M. Designing Nanosensors Based on Charged Derivatives of Gramicidin A. *J Am Chem Soc* 129, 9737-9745 (2007).

Chachin, M., Y. Katayama, Yamada, M., Horio, Y., Ohmura, T., Kitagawa, H., Uchida, S. and Kurachi, Y. Epinastine, a nonsedating histamine H"1 receptor antagonist, has a negligible effect on HERG channel. *European Journal of Pharmacology* 374(3): 457-460 (1999)

Cheley, S., Gu, L. Q. & Bayley, H. Stochastic sensing of nanomolar inositol 1,4,5-trisphosphate with an engineered pore. *Chemistry & biology* 9, 829-838 (2002).

Chen, J., Seebohm, G. and Sanguinetti, M. C. Position of aromatic residues in the S6 domain, not inactivation, dictates cisapride sensitivity of HERG and eag potassium channels. *Proceedings of the National Academy of Sciences* 99(19): 12461-12466 (2002)

Cheng, C. S., Alderman, D., Kwash, J., Dessaint, J., Patel, R., Lescoe, M K., Kinrade, M. B. and Weifeng, Y. A high-throughput HERG potassium channel function assay: An old assay with a new look. *Drug Development and Industrial Pharmacy* 28(2): 177-191 (2002)

Chiu, P. J. S., Marcoe, K. F., Bounds, S. E., Lin, C. H., Feng, J. J., Atsui, L., Cheng, F. C., Crumb, W. J. and Mitchell, R. Validation of a [3H]astemizole binding assay in HEK293 cells expressing HERG K+ channels. *Journal of Pharmacological Sciences* 95(3): 311-319 (2004)

Chuang, H., Neuhausser, W. M. and Julius, D. The super-cooling agent icilin reveals a mechanism of coincidence detection by a temperature-sensitive TRP channel. *Neuron*, 2004, 43, 859-869.

Cohen, F. S. Fusion of phospholipid vesicles with planar phospholipid bilayer membranes. II. Incorporation of a vesicular membrane marker into the planar membrane. *The Journal of General Physiology* 75, 251-270 (1980).

Colburn, R. W., Lubin, M. L., Stone, D. J., Wang, Y., Lawrence, D., D'Andrea, M. R., Brandt, M. R., Liu, Y. M., Flores, C. M. and Qin, N. Attenuated cold sensitivity in TRPM8 null mice. *Neuron*, 2007, 54, 379-386.

Comley, J. Patchers verses screener: divergent opinion on high throughput electrophysiology. *Drug Discovery World*, 47-57 (2003).

Diaz, G. J., Daniell, K., Leitza, S. T., Martin, R. L., Su, Z., McDermott, J. S., Cox, B. F. and Gintant, G. A. The [3H] dofetilide binding assay is a predictive screening tool for hERG blockade and proarrhythmia: Comparison of intact cell and membrane preparations and effects of altering [K+]. *Journal of Pharmacological and Toxicological Methods* 50(3): 187-199 (2004)

Dragoni, I., Guida, E. and McIntyre, P. The Cold and Menthol Receptor TRPM8 Contains a Functionally Important Double Cysteine Motif. *J. Biol. Chem.*, 2006, 281, 37353-37360.

Dunlop, J., Bowlby, M., Peri, R., Vasilyev, D. & Arias, R. High-throughput electrophysiology: an emerging paradigm for ion-channel screening and physiology. *Nature Reviews Drug Discovery* 7, 358-368 (2008).

Eccles, R. Methanol and related cooling compounds. *J. Pharm. Pharmacol.*, 1994, 46, 618-630.

El-Arabi, A. M., Salazar, C. S, and Schmidt, J. J. Ion channel drug potency assay with an artificial bilayer chip. *Lab on a Chip* 12(13): 2409-2413 (2012)

Falconer, M., Smith, F., Surah-Narwal S, Congrave G, Liu Z, Hayter P, Ciaramella G, Keighley W, Haddock P, Waldron G and Sewing A. High-Throughput Screening for Ion Channel Modulators. *Journal of Biomolecular Screening* 7(5): 460-465 (2002)

Fernández, J. A., Skryma, R., Bidaux, G., Magleby, K. L., Scholfield, C. N., McGeown, J. G., Prevarskaya, N. and Zholos, A. V. Voltage- and cold-dependent gating of single TRPM8 ion channels. *J. Gen. Physiol.*, 2011, 137, 173-195.

Funakoshi, K., Suzuki, H. & Takeuchi, S. Lipid bilayer formation by contacting monolayers in a microfluidic device for membrane protein analysis. *Anal Chem* 78, 8169-8174 (2006).

Golowasch, J., Kirkwood, A. and Moller, C. Allosteric effects of Mg2+ on the gating of Ca2+-activated K+ channels from mammalian skeletal muscle. *Journal of experimental biology* 124(1): 5-13 (1986)

Gu, L. Q., Braha, O., Conlan, S., Cheley, S. & Bayley, H. Stochastic sensing of organic analytes by a pore-forming protein containing a molecular adapter. *Nature* 398, 686-690 (1999).

Guan, X. Y., Gu, L. Q., Cheley, S., Braha, O. & Bayley, H. Stochastic sensing of TNT with a genetically engineered pore. *Chembiochem* 6, 1875-1881 (2005).

Han, X., Studer, A., Sehr, H., Geissbühler, I., DiBerardino, M., Winkler, F. K. and Tiefenauer, L. X. Nanopore Arrays for Stable and Functional Free-Standing Lipid Bilayers. *Adv. Mater.*, 2007, 19, 4466-4470.

Hancox, J. C., McPate, M. J., El Harchi, A. and Zhang, Y. H. The hERG potassium channel and hERG screening for drug-induced torsades de pointes. Pharmacology & therapeutics 119(2): 118-132 (2008)

Hanke, W. & Schlue, W. R. Planar Lipid Bilayers: Methods and Applications. Academic Press, London; New York (1993).

Heron, A. J., Thompson, J. R., Mason, A. E. & Wallace, M. I. Direct detection of membrane channels from gels using water-in-oil droplet bilayers. *J Am Chem Soc* 129, 16042-16047 (2007).

Hertzberg, R. P. & Pope, A. J. High-throughput screening: new technology for the 21st century. *Current Opinion in Chemical Biology* 4, 445-451 (2000).

Hirano, M., Kobayashi, T. and Ide, T. Lipid Bilayers at Gel/Gel Interface for Ion Channel Recordings. *J. Surf. Sci. Nanotechnol.*, 2008, 6, 130-133.

Holden, M. A., Needham, D. & Bayley, H. Functional bio-networks from nanoliter water droplets. *J Am Chem Soc* 129, 8650-8655 (2007).

Hromada, L. P., Nablo, B. J., Kasianowicz, J. J., Gaitan, M. A. & DeVoe, D. L. Single molecule measurements within individual membrane-bound ion channels using a polymer-based bilayer lipid membrane chip. *Lab on a Chip* 8, 602-608 (2008).

Hu, H. Z., Gu, Q., Wang, C., Colton, C. K., Tang, J., Kinoshita-Kawada, M., Lee, L. Y., Wood, J. D. and Zhu, M. X. 2-Aminoethoxydiphenyl borate is a common activator of TRPV1, TRPV2, and TRPV3. *J. Biol. Chem.*, 2004, 279, 35741-35748.

Hwang, W. L., Chen, M., Cronin, B., Holden, M. A. & Bayley, H. Asymmetric droplet interface bilayers. *J Am Chem Soc* 130, 5878-+(2008).

Ide, T., Kobayashi, T. and Hirano, M. Lipid Bilayers at the Gel Interface for Single Ion Channel Recordings. *Anal. Chem.*, 2008, 80, 7792-7795.

Jeon, T. J., Malmstadt, N. & Schmidt, J. J. Hydrogel-encapsulated lipid membranes. *J Am Chem Soc* 128, 42-43 (2006).

Jeon, T. J., Poulos, J. L. & Schmidt, J. J. Black lipid membranes stabilized through substrate conjugation to a hydrogel *Biointerphases* 3, 96-100 (2008).

Kang, X. F., Cheley, S., Rice-Ficht, A. C. & Bayley, H. A storable encapsulated bilayer chip containing a single protein nanopore. *J Am Chem Soc* 129, 4701-4705 (2007).

Kasianowicz, J., Brandin, E., Branton, D. & Deamer, D. W. Characterization of individual polynucleotide molecules using a membrane channel. *Proc. Natl. Acad. Sci. U.S.A.* 93, 13770-13773 (1996).

Keating, M. T. & Sanguinetti, M. C. Molecular and cellular mechanisms of cardiac arrhythmias. *Cell* 104, 569-580 (2001).

Kedei, N., Szabo, T., Lile, J. D., Treanor, J. J., Olah, Z. Z., Iadarola, M. J. and Blumberg, P. M. Analysis of the native quaternary structure of vanilloid receptor 1. *J. Biol. Chem.*, 2001, 276, 28613-28619.

Kiehn, J., Lacerda, A. E., Wible, B. and Brown, A. Cellular and Molecular Cardiology: Molecular Physiology and Pharmacology of HERG: Single-Channel Currents and Block by Dofetilide. *Circulation* 94(10): 2572-2579 (1996)

Lashinger, E. S. R., Steiginga, M. S., Hieble, J. P., Leon, L. A., Gardner, S. D., Nagilla, R., Davenport, E. A., Hoffman, B. E., Laping N. J. and Su, X. AMTB, a TRPM8 channel blocker: evidence in rats for activity in overactive bladder and painful bladder syndrome *Am. J. Physiol. Renal Physiol.*, 2008, 295, 803-810.

Le Pioufle, B., Suzuki, H., Tabata, K. V., Noji, H. & Takeuchi, S. Lipid bilayer microarray for parallel recording of transmembrane ion currents. *Anal Chem* 80, 328-332 (2008).

Leptihn S, T. J. R., Ellory J C, Tucker S J, Wallace M I In Vitro Reconstitution of Eukaryotic Ion Channels using Droplet Interface Bilayers. *J. Am. Chem. Soc.* 133 9370-9375 (2011).

Liu B. and Qin F. Functional control of cold- and menthol-sensitive TRPM8 ion channels by phosphatidylinositol 4,5-bisphosphate. *J. Neurosci.*, 2005, 25, 1674-1681.

Long, S. B., Tao, X., Campbell, E. B. and MacKinnon, R. Atomic structure of a voltage-dependent K+ channel in a lipid membrane-like environment. *Nature*, 2007, 450, 376-382.

Malmstadt, N., Jeon, T. J. & Schmidt, J. J. Long-lived Planar Lipid Bilayer Membranes Anchored to an In Situ Polymerized Hydrogel. *Advanced Materials* 20, 84-89 (2008).

Malmstadt, N., Nash, M. A., Purnell, R. F. & Schmidt, J. J. Automated formation of lipid-bilayer membranes in a microfluidic device. *Nano letters* 6, 1961-1965 (2006).

Mayer, M., Kriebel, J. K., Tosteson, M. T. & Whitesides, G. M. Microfabricated teflon membranes for low-noise recordings of ion channels in planar lipid bilayers. *Biophys J* 85, 2684-2695 (2003).

Mayer, M., Semetey, V., Gitlin, I., Yang, J. & Whitesides, G. M. Using ion channel-forming peptides to quantify protein-ligand interactions. *J Am Chem Soc* 130, 1453-1465 (2008).

McKemy, D. D., Neuhausser W. M. and Julius, D. Identification of a cold receptor reveals a general role for TRP channels in thermosensation. *Nature*, 2002, 416, 52-58.

Miller, C. Ion channel reconstitution. (Plenum Press, New York; 1986).

Molokanova, M. & Savchenko, A. Bright future of optical assays for ion channel drug discovery. *Drug Discovery Today* 13, 14-22 (2008).

Montal, M. & Mueller, P. Formation of bimolecular membranes from lipid monolayers and a study of their electrical properties. *Proceedings of the National Academy of Sciences of the United States of America* 69, 3561-3566 (1972).

Mueller, P., Rudin, D. O., Ti Tien, H. & Wescott, W. C. Reconstiution of Cell Membrane Structure in vitro and its Transformation into an Excitable System. *Nature* 194, 979-980 (1962).

Nilius, B. TRP channels in disease. *Biochimica Et Biophysica Acta-Molecular Basis of Disease* 1772, 805-812 (2007).

Ottova, A. L. & Tien, H. T. Self-assembled bilayer lipid membranes: from mimicking biomembranes to practical applications. *Bioelectrochemistry and Bioenergetics* 42, 141-152 (1997).

Peier, A. M., Moqrich, A., Hergarden, A. C., Reeve, A. J., Andersson, D. A., Story, G. M., Earley, T. J., Dragoni, I., McIntyre, P., Bevan S, and Patapoutian A. A TRP Channel that Senses Cold Stimuli and Menthol. *Cell,* 2002, 108, 705-715.

Perez, G., Lagrutta, A., Adelman, J. P. & Toro, L. Reconstitution of Expressed K—Ca Channels from *Xenopus*-Oocytes to Lipid Bilayers. *Biophys J* 66, 1022-1027 (1994).

Portonovo, S. A. and Schmidt, J. J. Masking apertures enabling automation and solution exchange in sessile droplet lipid bilayers. *Biomed. Microdevices,* 2011, DOI: 10.1007/s10544-011-9596-5.

Poulos, J. L. Jeon T. J., Damoiseaux R., Gillespie E. J., Bradley K. A. and Schmidt J. J. Ion channel and toxin measurement using a high throughput lipid membrane platform. *Biosensors & Bioelectronics* 24, 1806-1810 (2009).

Poulos, J. L., Bang, H., Jeon, T.-J. & Schmidt, J., J., Vol. 7035. (eds. R. Manijeh & M. Hooman) 703509 (SPIE, 2008).

Poulos, J. L., Jeon, T. J. and Schmidt, J. J. Automatable bilayer chips. *Biotechnol. J.,* 2010, 5, 511-514.

Poulos, J. L., Nelson, W. C., Jeon, T.-J., Kim, C.-J. & Schmidt, J. Electrowetting on dielectric-based microfluidics for integrated lipid bilayer formation and measurement. *Applied Physics Letters* 95, 013706 (2009).

Poulos, J. L., Portonovo, S. A., Bang, H. & Schmidt, J. J. Automatable lipid bilayer formation and ion channel measurement using sessile droplets. *J. Phys.: Condens. Matter* 22, 454105 (2010).

Purnell, R. F., Mehta, K. H. & Schmidt, J. J. Nucleotide identification and orientation discrimination of DNA homopolymers immobilized in a protein nanopores. *Nano-Letters,* DOI: 10.1021/n1802312f (2008).

Rohács, T., Lopes, C. M. B., Michailidis, I. and Logothetis, D. E. PI(4,5)P2 regulates the activation and desensitization of TRPM8 channels through the TRP domain. *Nat. Neurosci.,* 2005, 8, 626-634.

Rosenbaum, T., Awaya, M. and Gordon, S. E. Subunit modification and association in VR1 ion channels. *BMC Neurosci.* 2002, 3, 4-13.

Sakmann B. and Neher E. Patch clamp techniques for studying ionic channels in excitable membranes. *Ann. Rev. Physiol.,* 1984, 46, 455-472.

Sakmann, B. & Neher, E. (eds.) Single-channel recording. (Plenum Press, New York; 1995).

Sandison, M. E. & Morgan, H. Rapid fabrication of polymer microfluidic systems for the production of artificial lipid bilayers. *Journal of Micromechanics and Microengineering* 15, S139-S144 (2005).

Sandison, M. E., Zagnoni, M. & Morgan, H. Air-exposure technique for the formation of artificial lipid bilayers in microsystems. *Langmuir* 23, 8277-8284 (2007).

Sandison, M. E., Zagnoni, M., Abu-Hantash, M. & Morgan, H. Micromachined glass apertures for artificial lipid bilayer formation in a microfluidic system. *Journal of Micromechanics and Microengineering* 17, S189-S196 (2007).

Schein, S. J., Colombini, M. and Finkelstein, A. Reconstitution in planar lipid bilayers of a voltage-dependent anion-selective channel obtained from paramecium mitochondria. *Journal of Membrane Biology* 30(1): 99-120 (1976)

Schindler, H. and J. P. Rosenbusch Matrix Protein from *Escherichia coli* Outer Membranes Forms Voltage-Controlled Channels in Lipid Bilayers. *Proceedings of the National Academy of Sciences* 75(8): 3751-3755 (1978)

Schindler, H. and U. Quast Functional acetylcholine receptor from *Torpedo marmorata* in planar membranes. *Proceedings of the National Academy of Sciences* 77(5): 3052 (1980)

Schindler, H. Formation of Planar Bilayers from Artificial or Native Membrane-Vesicles. *Febs Letters* 122, 77-79 (1980).

Schmalhofer, Swensen, A. M., Thomas, B. S., Felix, J. P., Haedo, R. J., Solly, K., Kiss, L., Kaczorowski, G. J. and Garcia M. L. A Pharmacologically Validated, High-Capacity, Functional Thallium Flux Assay for the Human Ether-à-go-go Related Gene Potassium Channel. *Assay and drug development technologies* 8(6): 714-726 (2010)

Shim, J. W. & Gu, L. Q. Stochastic sensing on a modular chip containing a single-ion channel. *Anal Chem* 79, 2207-2213 (2007).

Suarezisla, B. A., Wan, K., Lindstrom, J. & Montal, M. Single-Channel Recordings from Purified Acetylcholine-Receptors Reconstituted in Bilayers Formed at the Tip of Patch Pipets. *Biochemistry* 22, 2319-2323 (1983).

Suzuki, H., Tabata, K., Kato-Yamada, Y., Noji, H. & Takeuchi, S. Planar lipid bilayer reconstitution with a microfluidic system. *Lab on a Chip* 4 (Advance Article) (2004).

Suzuki, H., Tabata, K. V., Noji, H. & Takeuchi, S. Electrophysiological recordings of single ion channels in planar lipid bilayers using a polymethyl methacrylate microfluidic chip. *Biosensors & Bioelectronics* 22, 1111-1115 (2007).

Suzuki, H., Tabata, K. V., Noji, H. & Takeuchi, S. Highly reproducible method of planar lipid bilayer reconstitution in polymethyl methacrylate microfluidic chip. *Langmuir* 22, 1937-1942 (2006).

Syeda, R., Holden, M. A., Hwang, W. L. & Bayley, H. Screening Blockers Against a Potassium Channel with a Droplet Interface Bilayer Array. *J Am Chem Soc* 130, 15543-15548 (2008).

Takagi, M., Azuma, K. & Kishimoto, U. A new method for the formation of bilayer membranes in aqueous solutions. *Annu. Rep. Biol. Fac. Sci. Osaka* 13, 107-110 (1965).

Tao, X. and MacKinnon, R. Functional analysis of Kv1.2 and paddle chimera Kv channels in planar lipid bilayers. *J. Mol. Biol.*, 2008, 382, 24-33.

Thapliyal, T., Poulos, J. L. and Schmidt, J. J. Automated lipid bilayer and ion channel measurement platform. *Biosens. Bioelectron.*, 2011, 26, 2651-2654.

Titus, S. A., Beacham D., Shahane, S. A., Southall, N., Xia, M., Huang, R., Hooten, E., Zhao, Y., Shou, L., Austin, C. P. and Zheng, W. A new homogeneous high-throughput screening assay for profiling compound activity on the human ether-a-go-go-related gene channel. *Analytical Biochemistry* 394(1): 30-38 (2009)

Tsavaler, L., Shapero, M. H., Morkowski, S, and Laus, R. Trp-p8, a novel prostate-specific gene, is up-regulated in prostate cancer and other malignancies and shares high homology with transient receptor potential calcium channel proteins. *Cancer Res.*, 2001, 61, 3760-3769.

Tsofina, L. M., Liberman, E. A. & Babakov, A. V. Production of Bimolecular Protein-Lipid Membranes in Aqueous Solution. *Nature* 212, 681-683 (1966).

Vodyanoy, I., Hall, J. E. & Balasubramanian, T. M. Alamethicin-Induced Current-Voltage Curve Asymmetry in Lipid Bilayers. *Biophys J* 42, 71-82 (1983).

White, S. H. The physical nature of planar bilayer membranes in *Ion Channel Reconstitution*, Plenum Press, New York, 1986.

Wonderlin, W. F., Finkel, A. & French, R. J. Optimizing Planar Lipid Bilayer Single-Channel Recordings for High-Resolution with Rapid Voltage Steps. *Biophys J* 58, 289-297 (1990).

Wong, D., Jeon, T. J. & Schmidt, J. Single molecule measurements of channel proteins incorporated into biomimetic polymer membranes. *Nanotechnology* 17, 3710-3717 (2006).

Wulff, H., Castle, N. A. and Pardo, L. A. Voltage-gated potassium channels as therapeutic targets. *Nature Reviews Drug Discovery* 8(12): 982-1001 (2009)

Yuan, C., O'Connell, R. J., Feinberg-Zadek, P. L., Johnston, L. J. and Treistman, S. N. Bilayer Thickness Modulates the Conductance of the BK Channel in Model Membranes. *Biophysical journal* 86(6): 3620-3633 (2004)

Zagnoni M., Sandison, M. E., Marius, P. and Morgan, H., 2009. Bilayer lipid membranes from falling droplets. *Anal. Bioanal. Chem.* 393, 1601-1605.

Zagnoni, M., Sandison, M. E. and Morgan, H. Microfluidic array platform for simultaneous lipid bilayer membrane formation. *Biosens. Bioelectron.*, 2009, 24, 1235-1240.

Zakharian, E., Cao, C. and Rohacs, T. Gating of Transient Receptor Potential Melastatin 8 (TRPM8) Channels Activated by Cold and Chemical Agonists in Planar Lipid Bilayers. *J. Neurosci.*, 2010, 30, 12526-12534.

Zakharian, E., Thyagarajan, B., French, R. J., Pavlov, E. and Rohacs, T. Inorganic polyphosphate modulates TRPM8 channels. *PLoS One*, 2009, 4, e5404.

Zhang, L. and Barritt, G. J. TRPM8 in prostate cancer cells: a potential diagnostic and prognostic marker with a secretory function? *Endocr. Relat. Cancer*, 2006, 13, 27-38.

Zholos, A. Pharmacology of transient receptor potential melastatin channels in the vasculature. *Brit. J. Pharmacol.*, 2010, 159, 1559-1571.

Zhou, Z., Gong, Q., Ye, B., Fan, Z., Makielski, J. C., Robertson, G. A. and January, C. T. Properties of HERG channels stably expressed in HEK 293 cells studied at physiological temperature. *Biophysical journal* 74(1): 230-241 (1998)

Zou, A., Curran, M. E., Keating, M. T. and Sanguinetti, M. C. Single HERG delayed rectifier K+ channels expressed in *Xenopus* oocytes. *American Journal of Physiology-Heart and Circulatory Physiology* 272(3): H1309-H1314 (1997)

What is claimed is:

1. A method of making a lipid bilayer comprising:
a) providing a device comprising a substrate defining at least one aperture;
b) providing a first solution on one side of the aperture;
c) providing a second solution on the opposite side of the aperture from the first solution, wherein the first solution is immiscible in the second solution;
d) providing a first amphiphilic molecule in the first solution, or second solution, or in both the first solution and second solution;
e) contacting the first solution and the second solution through the aperture, thereby forming a first amphiphilic molecule monolayer;
f) providing a fourth solution;
g) providing a second amphiphilic molecule in the second solution, or fourth solution, or in both the second solution and fourth solution;
h) submerging at least a portion of the fourth solution in the second solution, wherein the fourth solution is immiscible in the second solution, thereby forming a second amphiphilic molecule monolayer; and
i) contacting the second amphiphilic molecule monolayer and the first amphiphilic molecule monolayer, thereby forming an amphiphilic molecule bilayer.

2. The method of claim 1, wherein the amphiphilic molecule bilayer is a lipid bilayer.

3. The method of claim 1, wherein the method further comprises performing a measurement selected from an electrical measurement, an optical measurement, a chemical measurement, and an acoustic measurement, or a combination thereof.

4. The method of claim 1, wherein the first solution is an aqueous solution.

5. The method of claim 1, wherein the second solution is a non-aqueous solution.

6. The method of claim 1, wherein the amphiphilic molecule bilayer comprises one or more ion channels, one or more receptors, or one or more membrane proteins, or a mixture thereof.

7. A method of performing electrical measurements on an amphiphilic molecule bilayer comprising:
   providing an amphiphilic molecule bilayer formed at an aperture; and
   performing an electrical measurement,
wherein providing an amphiphilic molecule bilayer formed at an aperture comprises:
   a) providing a device comprising a substrate defining at least one aperture;
   b) providing a first solution on one side of the aperture;
   c) providing a second solution on the opposite side of the aperture from the first solution, wherein the first solution is immiscible in the second solution;
   d) providing a first amphiphilic molecule in the first solution, or second solution, or in both the first solution and second solution;
   e) contacting the first solution and the second solution through the aperture, thereby forming a first amphiphilic molecule monolayer;
   f) providing a fourth solution;
   g) providing a second amphiphilic molecule in the second solution, or fourth solution, or in both the second solution and fourth solution;
   h) submerging at least a portion of the fourth solution in the second solution, wherein the fourth solution is immiscible in the second solution, thereby forming a second amphiphilic molecule monolayer; and
   i) contacting the second amphiphilic molecule monolayer and the first amphiphilic molecule monolayer, thereby forming an amphiphilic molecule bilayer.

\* \* \* \* \*